(12) United States Patent
Karasawa

(10) Patent No.: US 9,669,626 B2
(45) Date of Patent: Jun. 6, 2017

(54) LIQUID EJECTION CONTROL APPARATUS, LIQUID EJECTION SYSTEM, AND CONTROL METHOD

(71) Applicant: SEIKO EPSON CORPORATION, Tokyo (JP)

(72) Inventor: Junichi Karasawa, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/268,570

(22) Filed: Sep. 17, 2016

(65) Prior Publication Data

US 2017/0080711 A1   Mar. 23, 2017

(30) Foreign Application Priority Data

Sep. 18, 2015  (JP) ................. 2015-185398

(51) Int. Cl.
*A61B 17/3203* (2006.01)
*B41J 2/045* (2006.01)
*A61B 17/00* (2006.01)

(52) U.S. Cl.
CPC ....... *B41J 2/04588* (2013.01); *A61B 17/3203* (2013.01); *A61B 17/32037* (2013.01); *B41J 2/04581* (2013.01); *A61B 2017/00017* (2013.01); *A61B 2017/0019* (2013.01); *A61B 2017/00154* (2013.01); *A61B 2017/00181* (2013.01); *A61B 2017/00185* (2013.01)

(58) Field of Classification Search
CPC ............... B41J 2/04588; B41J 2/04581; A61B 17/3203; A61B 17/32037; A61B 2017/00017; A61B 2017/00181; A61B 2017/00185; A61B 2017/0019; A61B 2017/00154

See application file for complete search history.

(56) References Cited

U.S. PATENT DOCUMENTS

| 9,289,228 B2 | 3/2016 | Seto et al. |
| 2015/0073452 A1* | 3/2015 | Uchida ............... A61B 17/3203 606/167 |

(Continued)

FOREIGN PATENT DOCUMENTS

| JP | 2005-152127 A | 6/2005 |
| JP | 2009-039384 A | 2/2009 |

(Continued)

*Primary Examiner* — Julian Huffman
(74) *Attorney, Agent, or Firm* — Maschoff Brennan

(57) ABSTRACT

In a liquid ejection control apparatus, an operation unit includes an energy dial used to input an energy indication value related to kinetic energy of a pulsed liquid jet ejected from a liquid ejection device, and a repetition frequency dial used to input a repetition frequency indication value related to the number of times of ejection per unit time of the pulsed liquid jet. A control unit includes a rising waveform shape setting section which sets a rising waveform shape of a drive voltage waveform so that the kinetic energy has the energy indication value on the basis of voltage amplitude of the drive voltage waveform and the repetition frequency indication value. The repetition frequency dial may be omitted, and a repetition frequency may be fixed to a predetermined value.

15 Claims, 25 Drawing Sheets

(56) References Cited

U.S. PATENT DOCUMENTS

| | | |
|---|---|---|
| 2015/0224527 A1 | 8/2015 | Kojima et al. |
| 2016/0185106 A1 | 6/2016 | Karasawa |
| 2016/0185107 A1 | 6/2016 | Karasawa |
| 2016/0185108 A1 | 6/2016 | Karasawa |
| 2016/0185109 A1 | 6/2016 | Karasawa |
| 2016/0221335 A1 | 8/2016 | Karasawa |
| 2016/0221336 A1 | 8/2016 | Karasawa |

FOREIGN PATENT DOCUMENTS

| | | |
|---|---|---|
| JP | 2011-036533 A | 2/2011 |
| JP | 2016-016284 A | 2/2016 |
| JP | 2016-027838 A | 2/2016 |
| JP | 2016-120023 A | 7/2016 |
| JP | 2016-120024 A | 7/2016 |
| JP | 2016-120066 A | 7/2016 |
| JP | 2016-120067 A | 7/2016 |
| JP | 2016-140551 A | 8/2016 |
| JP | 2016-140552 A | 8/2016 |

* cited by examiner

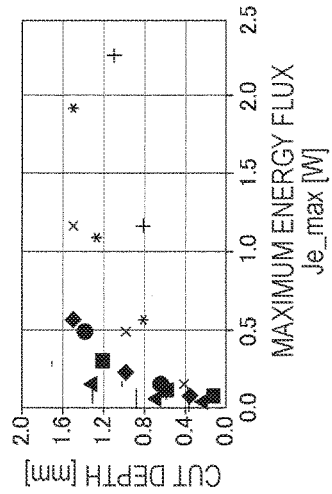
FIG. 6E
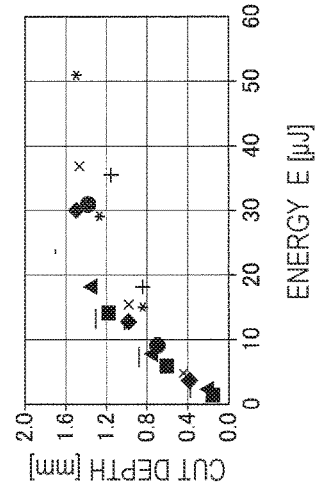
FIG. 6F
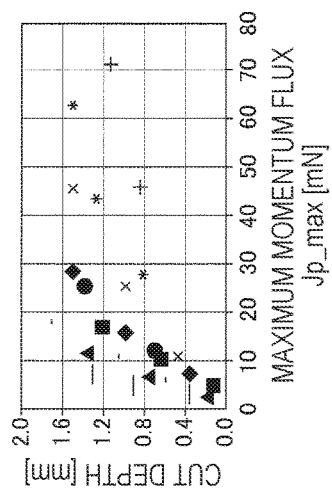
FIG. 6C
FIG. 6D
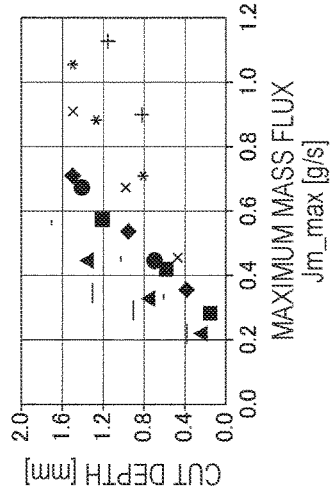
FIG. 6A
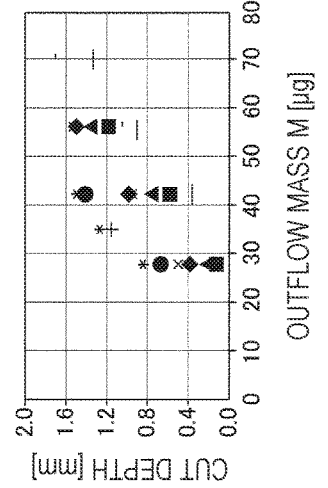
FIG. 6B

FIG. 18

| ENERGY DIAL POSITION | ENERGY INDICATION VALUE | REPETITION FREQUENCY DIAL POSITION | REPETITION FREQUENCY INDICATION VALUE | RISING WAVEFORM SHAPE |
|---|---|---|---|---|
| 1 | E_001 | 1 | F_001 | WS_011 |
|   |       | 2 | F_002 | WS_012 |
|   |       | 3 | F_003 | WS_013 |
|   |       | 4 | F_004 | WS_014 |
|   |       | 5 | F_005 | WS_015 |
| 2 | E_002 | 1 | F_001 | WS_021 |
|   |       | 2 | F_002 | WS_022 |
|   |       | 3 | F_003 | WS_023 |
|   |       | 4 | F_004 | WS_024 |
|   |       | 5 | F_005 | WS_025 |
| 3 | E_003 | 1 | F_001 | WS_031 |
|   |       | 2 | F_002 | WS_032 |
|   |       | 3 | F_003 | WS_033 |
|   |       | 4 | F_004 | WS_034 |
|   |       | 5 | F_005 | WS_035 |
| 4 | E_004 | 1 | F_001 | WS_041 |
|   |       | 2 | F_002 | WS_042 |
|   |       | 3 | F_003 | WS_043 |
|   |       | 4 | F_004 | WS_044 |
|   |       | 5 | F_005 | WS_045 |
| 5 | E_005 | 1 | F_001 | WS_051 |
|   |       | 2 | F_002 | WS_052 |
|   |       | 3 | F_003 | WS_053 |
|   |       | 4 | F_004 | WS_054 |
|   |       | 5 | F_005 | WS_055 |

771

| ENERGY DIAL POSITION | ENERGY INDICATION VALUE | REPETITION FREQUENCY DIAL POSITION | REPETITION FREQUENCY INDICATION VALUE | VOLTAGE AMPLITUDE DIAL POSITION | VOLTAGE AMPLITUDE INDICATION VALUE | RISING WAVEFORM SHAPE |
|---|---|---|---|---|---|---|
| 1 | E_001 | 1 | F_001 | 1 | V_011 | WS_111 |
|   |   |   |   | 2 | V_012 | WS_112 |
|   |   |   |   | 3 | V_013 | WS_113 |
|   |   |   |   | 4 | V_014 | WS_114 |
|   |   |   |   | 5 | V_015 | WS_115 |
|   |   | 2 | F_002 | 1 | V_011 | WS_121 |
|   |   |   |   | 2 | V_012 | WS_122 |
|   |   |   |   | 3 | V_013 | WS_123 |
|   |   |   |   | 4 | V_014 | WS_124 |
|   |   |   |   | 5 | V_015 | WS_125 |
|   |   | ... | ... | ... | ... | ... |
|   |   | 5 | F_005 | 1 | V_011 | WS_151 |
|   |   |   |   | 2 | V_012 | WS_152 |
|   |   |   |   | 3 | V_013 | WS_153 |
|   |   |   |   | 4 | V_014 | WS_154 |
|   |   |   |   | 5 | V_015 | WS_155 |
| 2 | E_002 | 1 | F_001 | 1 | V_011 | WS_211 |
|   |   |   |   | 2 | V_012 | WS_212 |
|   |   |   |   | 3 | V_013 | WS_213 |
|   |   |   |   | 4 | V_014 | WS_214 |
|   |   |   |   | 5 | V_015 | WS_215 |
|   |   | ... | ... | ... | ... | ... |
|   |   | 5 | F_005 | 1 | V_011 | WS_251 |
|   |   |   |   | 2 | V_012 | WS_252 |
|   |   |   |   | 3 | V_013 | WS_253 |
|   |   |   |   | 4 | V_014 | WS_254 |
|   |   |   |   | 5 | V_015 | WS_255 |
| ... | ... | ... | ... | ... | ... | ... |

| ENERGY DIAL POSITION | ENERGY INDICATION VALUE | REPETITION FREQUENCY DIAL POSITION | REPETITION FREQUENCY INDICATION VALUE | VOLTAGE AMPLITUDE DIAL POSITION | VOLTAGE AMPLITUDE INDICATION VALUE | RISING FREQUENCY DIAL POSITION | RISING FREQUENCY INDICATION VALUE | RISING WAVEFORM SHAPE |
|---|---|---|---|---|---|---|---|---|
| 1 | E_001 | 1 | F_001 | 1 | V_011 | 1 | f_011 | WS_1111 |
| | | | | | | 2 | f_012 | WS_1112 |
| | | | | | | 3 | f_013 | WS_1113 |
| | | | | | | 4 | f_014 | WS_1114 |
| | | | | | | 5 | f_015 | WS_1115 |
| | | | | ... | ... | ... | ... | ... |
| | | | | 5 | V_015 | 1 | f_011 | WS_1151 |
| | | | | | | 2 | f_012 | WS_1152 |
| | | | | | | 3 | f_013 | WS_1153 |
| | | | | | | 4 | f_014 | WS_1154 |
| | | | | | | 5 | f_015 | WS_1155 |
| | | | | ... | ... | ... | ... | ... |
| | | 5 | F_005 | 1 | V_011 | 1 | f_011 | WS_1511 |
| | | | | | | 2 | f_012 | WS_1512 |
| | | | | | | 3 | f_013 | WS_1513 |
| | | | | | | 4 | f_014 | WS_1514 |
| | | | | | | 5 | f_015 | WS_1515 |
| | | | | ... | ... | ... | ... | ... |
| | | | | 5 | V_015 | 1 | f_011 | WS_1551 |
| | | | | | | 2 | f_012 | WS_1552 |
| | | | | | | 3 | f_013 | WS_1553 |
| | | | | | | 4 | f_014 | WS_1554 |
| | | | | | | 5 | f_015 | WS_1555 |
| ... | ... | ... | ... | ... | ... | ... | ... | ... |

LIQUID EJECTION CONTROL APPARATUS, LIQUID EJECTION SYSTEM, AND CONTROL METHOD

BACKGROUND

1. Technical Field

The present invention relates to a liquid ejection control apparatus and the like controlling a liquid ejection device which ejects a liquid in a pulse form by using a piezoelectric element.

2. Related Art

There is a technique of cutting a cutting target object by ejecting a liquid in a pulse form. The liquid ejected in a pulse form is a liquid jet flow which is ejected from a nozzle in a pulsating manner, and is referred to as a "pulsed liquid jet" as appropriate in the present specification.

A pulsed liquid jet may be variously applied, and, for example, JP-A-2005-152127 has proposed a technique in which the pulsed liquid jet is used for surgery in a medical field. In this case, a cutting target object is living tissue, and a liquid is physiological saline.

As one of the mechanisms generating a pulsed liquid jet, there is a mechanism using a piezoelectric element. The mechanism applies a pulsed drive voltage to a piezoelectric element so that the piezoelectric element generates instantaneous pressure in a working fluid (liquid), and thus ejects the liquid in a pulse form. Thus, the strength of the pulsed liquid jet is changed by controlling a drive voltage applied to the piezoelectric element. Therefore, there may be a technique in which a characteristic value of a drive voltage applied to a piezoelectric element, for example, the amplitude (which is voltage amplitude and can be said to the magnitude of the drive voltage) of a drive voltage waveform is indicated by using an operation portion such as an operation dial or an operation button, and thus the strength of a pulsed liquid jet is changed.

However, it has been found that, even if the characteristic value of the drive voltage indicated by the operation portion is changed, there is a case where a cutting aspect such as a cut depth or a cut volume of a cutting target object may not be changed as intended by a user. As will be described later in detail, it has been found that, for example, even if the user changes the voltage amplitude to twice or four times, or a half or a quarter, a cut depth or a cut volume is not necessarily changed in proportion thereto. In a case where a pulsed liquid jet is used for surgery, there may be a problem in that working corresponding to an operator's operation sense is not performed.

On the other hand, if an ejection cycle of the pulsed liquid jet is variable, a cut depth or a cut volume per unit time can be changed, and thus it is possible to adjust speed for cutting a cutting target object. However, if the ejection cycle is changed, a shape of a drive voltage waveform is changed, and thus the strength of a liquid jet corresponding to a single pulse may be changed. As a result, a cut depth or a cut volume related to a pulsed liquid jet corresponding to a single pulse is changed before and after an ejection cycle is changed, and thus a cutting speed proportional to an ejection frequency as intended by a user may not be obtained even if an ejection cycle is shortened, that is, an ejection frequency is heightened.

SUMMARY

An advantage of some aspects of the invention is to provide a technique capable of setting the strength of a pulsed liquid jet as intended by a user so as to improve convenience.

A first aspect of the invention is directed to a liquid ejection control apparatus which applies a predetermined drive voltage waveform to a piezoelectric element, and controls repeated ejection of a pulsed liquid jet from a liquid ejection device which ejects a liquid in a pulse form by using the piezoelectric element, the apparatus including a first operation unit that is used to input a first indication value related to kinetic energy of the pulsed liquid jet; and a control unit that controls the drive voltage waveform, and changes a waveform shape (hereinafter, referred to as a "rising waveform shape") related to rising of the drive voltage waveform so that the kinetic energy has the first indication value.

As another aspect of the invention, the invention may be configured as a control method of applying a predetermined drive voltage waveform to a piezoelectric element, and controlling repeated ejection of a pulsed liquid jet from a liquid ejection device which ejects a liquid in a pulse form by using the piezoelectric element, the method including inputting a first indication value related to kinetic energy of the pulsed liquid jet; and changing a waveform shape related to rising of the drive voltage waveform so that the kinetic energy has the first indication value.

According to the first aspect and the like of the invention, if the first indication value related to the kinetic energy of the pulsed liquid jet is input, a waveform shape related to rising of the drive voltage waveform is changed so that the kinetic energy has the first indication value. As will be described later, a cut depth or a cut volume is highly correlated with the kinetic energy of a pulsed liquid jet. Thus, if the kinetic energy of the pulsed liquid jet is directly indicated, a cut depth or a cut volume suitable for a user's intention or operation sense can be obtained, and thus it is possible to improve convenience.

A second aspect of the invention is directed to the liquid ejection control apparatus of the first aspect of the invention, which further includes a second operation unit that is used to input a second indication value related to the number of times of ejection per unit time of the pulsed liquid jet, and in which the control unit controls the drive voltage waveform so that the number of times of ejection per unit time of the pulsed liquid jet becomes the second indication value.

According to the second aspect of the invention, it is possible to indicate the number of times of ejection per unit time of a pulsed liquid jet. Consequently, for example, it is possible to change the number of times of ejection while maintaining the first indication value. Of course, even if the number of times of ejection is changed, a waveform shape related to rising of the drive voltage waveform is controlled so that the kinetic energy has the first indication value. Therefore, it is possible to adjust a cutting speed in a state in which a cut depth or a cut volume related to a pulsed liquid jet corresponding to a single pulse is not changed before and after the number of times of ejection is changed, and thus it is also possible to improve convenience.

A third aspect of the invention is directed to the liquid ejection control apparatus of the first or second aspect of the invention, which further includes a third operation unit that is used to input a third indication value related to voltage amplitude of the drive voltage waveform, and in which the control unit controls the voltage amplitude of the drive voltage waveform on the basis of the third indication value.

According to the third aspect of the invention, it is possible to indicate the voltage amplitude of the drive voltage waveform.

A fourth aspect of the invention is directed to the liquid ejection control apparatus of any one of the first to third aspects of the invention, which further includes a fourth operation unit that is used to input a fourth indication value related to a rising time of the drive voltage waveform, and in which the control unit controls the rising time of the drive voltage waveform on the basis of the fourth indication value.

According to the fourth aspect of the invention, it is possible to indicate the rising time of the drive voltage waveform.

A fifth aspect of the invention is directed to the liquid ejection control apparatus of any one of the first to fourth aspects of the invention, which further includes a display control unit that performs control of displaying the first indication value.

According to the fifth aspect of the invention, it is possible to display the first indication value related to the kinetic energy of a pulsed liquid jet. Consequently, it is possible to visually recognize the present kinetic energy of a pulsed liquid jet, indicated by a user. Therefore, it is possible to further improve convenience.

A sixth aspect of the invention is directed to the liquid ejection control apparatus of any one of the first to fifth aspects of the invention, in which the control unit controls the liquid ejection device so that momentum of the pulsed liquid jet is equal to or more than 2 nanonewton seconds (nNs) and is equal to or less than 2 millinewton seconds (mNs), or kinetic energy of the pulsed liquid jet is equal to or more than 2 nanojoules (nJ) and is equal to or less than 200 millijoules (mJ).

According to the sixth aspect of the invention, it is possible to control the liquid ejection device within a range in which the momentum of the pulsed liquid jet is equal to or more than 2 nNs and is equal to or less than 2 mNs, or the kinetic energy thereof is equal to or more than 2 nJ and is equal to or less than 200 mJ. Therefore, for example, the liquid ejection control apparatus is suitable to cut soft materials, for example, living tissue, food, a gel material, and a resin material such as rubber or plastic.

A seventh aspect of the invention is directed to the liquid ejection control apparatus of any one of the first to sixth aspects of the invention, in which the liquid ejection device is controlled so that living tissue is cut with the pulsed liquid jet.

According to the seventh aspect of the invention, it is possible to control the strength of a pulsed liquid jet suitable for surgery, for example.

An eighth aspect of the invention is directed to a liquid ejection system including the liquid ejection control apparatus according to any one of the first to seventh aspects of the invention; a liquid ejection device; and a liquid feeding pump.

According to the eighth aspect of the invention, it is possible to implement the liquid ejection system achieving the operations and effects of the first to seventh aspects of the invention.

BRIEF DESCRIPTION OF THE DRAWINGS

The invention will be described with reference to the accompanying drawings, wherein like numbers reference like elements.

FIGS. 6A to 6F are diagrams illustrating simulation results (cut depths).

FIG. 18 is a diagram illustrating a data configuration example of an energy conversion table in Embodiment 1.

FIG. 22 is a diagram illustrating a data configuration example of an energy conversion table in Embodiment 2.

FIG. 26 is a diagram illustrating a data configuration example of an energy conversion table in Embodiment 3.

DESCRIPTION OF EXEMPLARY EMBODIMENTS

Figure 1:
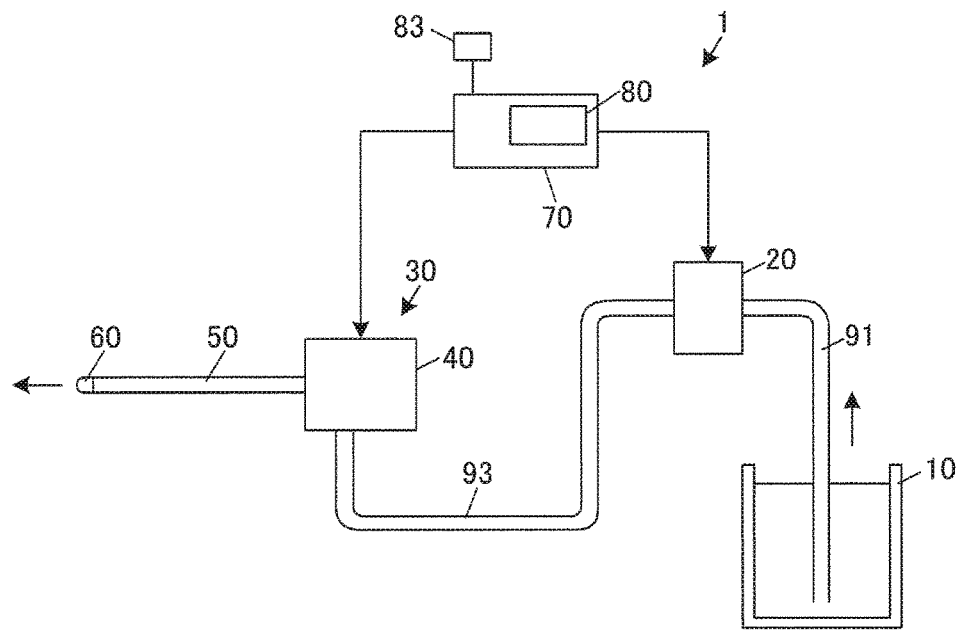
FIG. 1 is a diagram illustrating the entire configuration example of a liquid ejection system.

Hereinafter, a description will be made of embodiments of a liquid ejection control apparatus, a liquid ejection system, and a control method according to the invention. The invention is not limited to the embodiments described below, and embodiments to which the invention is applicable are not limited to the embodiments described below. The same portions are given the same reference numerals throughout the drawings.

Entire Configuration

FIG. 1 is a diagram illustrating the entire configuration example of a liquid ejection system 1 in the present embodiment. The liquid ejection system 1 is used for applications such as surgery with a soft material, for example, living tissue as a cutting target object, food processing with food as a cutting target object, processing of a gel material, and cutting processing of a resin material such as rubber or plastic, and ejects a pulsed liquid jet whose momentum is equal to or more than 2 nanonewton seconds (nNs) and is equal to or less than 2 millinewton seconds (mNs), or whose kinetic energy is equal to or more than 2 nanojoules (nJ) and is equal to or less than 200 millijoules (mJ) so as to cut a cutting target object. Hereinafter, a case will be exemplified in which the liquid ejection system 1 is used for a surgery application and performs incision, excision, or crushing (these are collectively referred to as "cutting") of the affected part (living tissue). Momentum flux and momentum in the present embodiment indicate a scalar quantity in which only an ejection direction component of a pulsed liquid jet, that is, the magnitude thereof is taken into consideration.

As illustrated in FIG. 1, the liquid ejection system 1 includes a container 10 accommodating a liquid, a liquid feeding pump device 20, a liquid ejection device 30 which ejects the liquid toward a cutting target object (living tissue in the present embodiment) in a pulse form, and a liquid ejection control apparatus 70.

In the liquid ejection system 1, the liquid ejection control apparatus 70 is provided with an operation panel 80 which is operated by an operator during surgery. The operation panel 80 is used to input various operations such as an operation of changing kinetic energy. The liquid ejection control apparatus 70 is provided with an ejection pedal 83 for switching between ejection starting and ejection stoppage of a pulsed liquid jet by the operator treading thereon.

The container 10 accommodates a liquid such as water, physiological saline, or a chemical liquid. The liquid feeding pump device 20 supplies the liquid accommodated in the container 10 to a pulse flow generator 40 of the liquid ejection device 30 at predetermined pressure or a predetermined flow rate via connection tubes 91 and 93.

The liquid ejection device 30 is a portion (handpiece) operated by the operator holding in hand during surgery, and includes the pulse flow generator 40 which gives pulsation to the liquid supplied from the liquid feeding pump 20 so as to generate a pulse flow, and a pipe-shaped ejection tube 50. The liquid ejection device 30 ejects the pulse flow generated by the pulse flow generator 40 from a liquid ejection opening 61 (refer to FIG. 2) provided at a nozzle 60 through the ejection tube 50 as a pulsed liquid jet.

Here, the pulse flow indicates a pulsative flow of the liquid which considerably and rapidly changes temporally in a flow velocity or pressure thereof. Similarly, ejecting a liquid in a pulse form indicates pulsative ejection of the liquid in which a flow velocity of the liquid passing through the nozzle considerably changes temporally. In the present embodiment, a case of ejecting a pulsed liquid jet generated by applying periodic pulsation to a steady flow is exemplified, but the invention is also applicable to intermittent and fitful ejection of a pulsed liquid jet in which ejection and non-ejection of a liquid are repeatedly performed.

Figure 2:
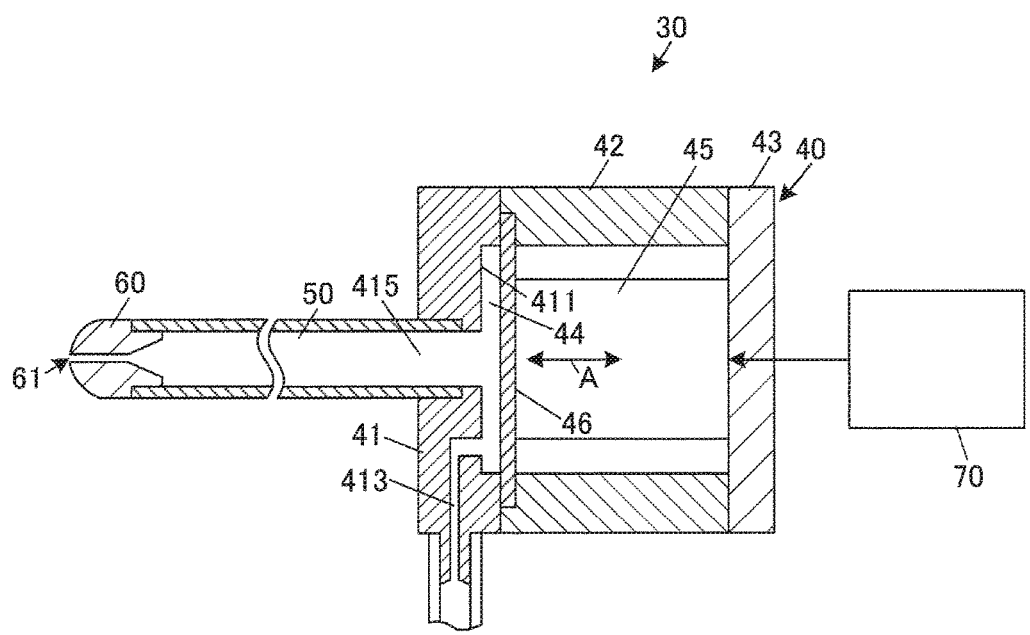
FIG. 2 is a diagram illustrating an internal structure of a liquid ejection device.

FIG. 2 is a diagram illustrating a cut surface obtained by cutting the liquid ejection device 30 along a liquid ejection direction. Vertical and horizontal scales of members or portions illustrated in FIG. 2 are different from actual ones for convenience of illustration. As illustrated in FIG. 2, the pulse flow generator 40 is configured of a piezoelectric element 45 and a diaphragm 46 which change a volume of a pressure chamber 44 and are disposed in a tubular internal space formed by a first case 41, a second case 42, and a third case 43. The respective cases 41, 42 and 43 are joined together and are thus integrally formed at surfaces facing each other.

The diaphragm 46 is a disk-shaped metal thin plate, and an outer circumferential portion thereof is interposed and fixed between the first case 41 and the second case 42. The piezoelectric element 45 is, for example, a laminated piezoelectric element, and has one end fixed to the diaphragm 46 between the diaphragm 46 and the third case 43, and the other end fixed to the third case.

The pressure chamber 44 is a space surrounded by the diaphragm 46, and a depression 411 formed on a surface of the first case 41 facing the diaphragm 46. The first case 41 is provided with an inlet channel 413 and an outlet channel 415 which communicate with the pressure chamber 44. An inner diameter of the outlet channel 415 is larger than an inner diameter of the inlet channel 413. The inlet channel 413 is connected to the connection tube 93 and introduces a liquid supplied from the liquid feeding pump device 20 into the pressure chamber 44. One end of the ejection tube 50 is connected to the outlet channel 415, and thus the liquid flowing in the pressure chamber 44 is introduced into the ejection tube 50. The nozzle 60 having a liquid ejection opening 61 which has an inner diameter smaller than an inner diameter of the ejection tube 50 is inserted into the other end (front end) of the ejection tube 50.

In the liquid ejection system 1 configured in the above-described way, the liquid accommodated in the container 10 is supplied to the pulse flow generator 40 via the connection tube 93 at predetermined pressure or a predetermined flow rate by the liquid feeding pump device 20 under the control of the liquid ejection control apparatus 70. On the other hand, if a drive signal is applied to the piezoelectric element 45 under the control of the liquid ejection control apparatus 70, and thus the piezoelectric element 45 is expanded or contracted (an arrow A in FIG. 2). The drive signal applied to the piezoelectric element 45 is repeatedly applied at a predetermined repetition frequency (for example, several tens of Hz to several hundreds of Hz), and thus expansion and contraction of the piezoelectric element 45 are repeatedly performed for each cycle. Consequently, pulsation is applied to the steady flow liquid flowing in the pressure chamber 44, and thus a pulsed liquid jet is repeatedly ejected from the liquid ejection opening 61.

Figure 3A:
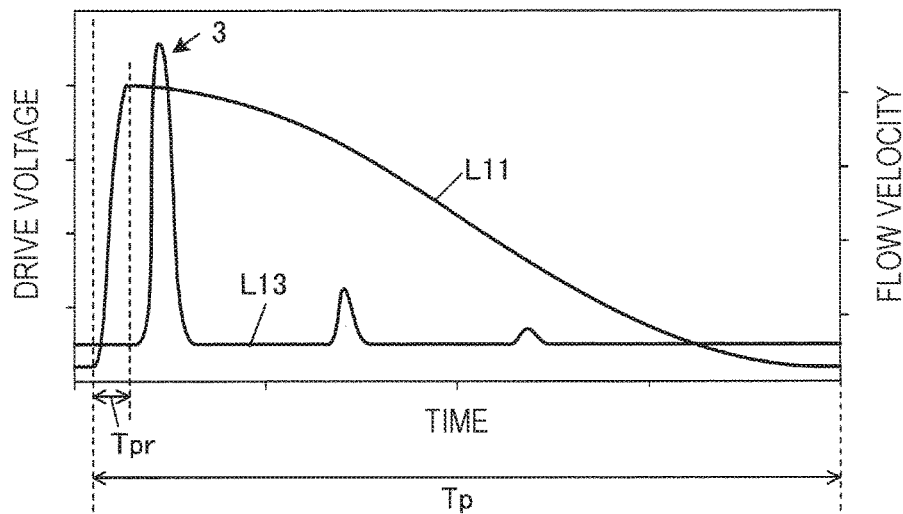
FIGS. 3A and 3B are diagrams illustrating a drive voltage waveform for a piezoelectric element corresponding to one cycle and a liquid flow velocity waveform in a liquid ejection opening.
Figure 3B:
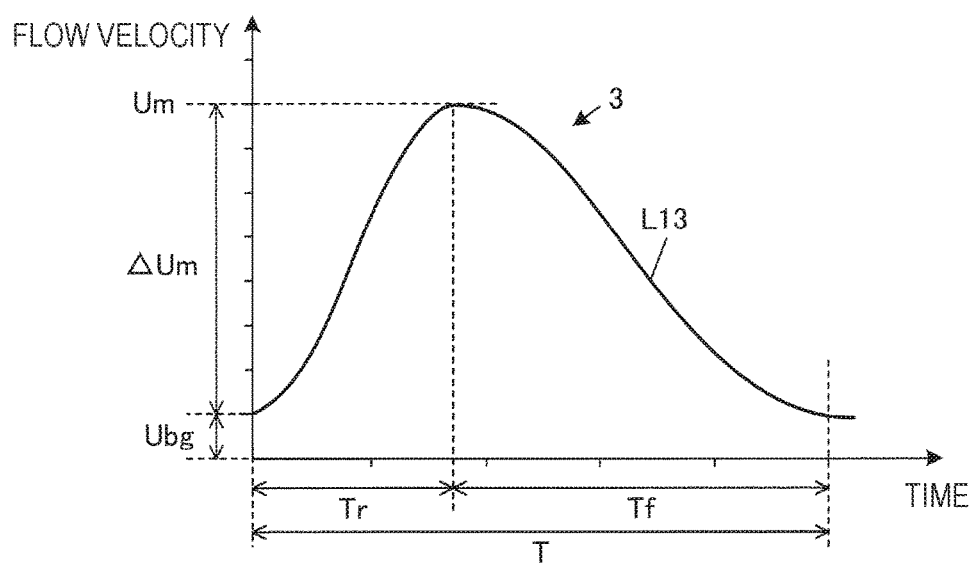

FIG. 3A is a diagram illustrating an example of a driving voltage waveform L11 of a drive signal corresponding to one cycle applied to the piezoelectric element 45, and also illustrates a flow velocity waveform L13 of a liquid in the liquid ejection opening 61. FIG. 3B is a diagram obtained by extracting a main jet 3 which is a flow velocity waveform (main peak portion) with the highest peak of peaks of the flow velocity waveform L13 illustrated in FIG. 3A.

In FIG. 3A, Tp illustrated in FIG. 3A indicates a repetition cycle (time corresponding to one cycle of a drive voltage waveform), and an inverse number thereof is the above-described repetition frequency. The repetition cycle Tp is about 1 millisecond (ms) to 100 ms, and time (rising time) Tpr for the drive voltage waveform to rise to the maximum voltage is 10 microseconds (μs) to 1000 μs. The repetition cycle Tp is set to be longer than the rising time Tpr. In a case where an inverse number of the rising time Tpr is a rising frequency, the repetition frequency is set to be lower than the rising frequency. Both of the rising frequency and the rising time are rising time indexes related to rising time of the drive voltage. Hereinafter, the rising frequency will be described as a representative example of an index value related to rising time.

For example, if the piezoelectric element 45 is expanded when a positive voltage is applied thereto, the piezoelectric element 45 is rapidly expanded at the rising time Tpr, and thus the diaphragm 46 is pushed by the piezoelectric element 45 so as to be bent toward the pressure chamber 44 side. If the diaphragm 46 is bent toward the pressure chamber 44 side, the volume of the pressure chamber 44 is reduced, and thus the liquid in the pressure chamber 44 is pushed out of the pressure chamber 44. Here, the inner diameter of the outlet channel 415 is larger than the inner diameter of the inlet channel 413, fluid inertance and fluid resistance of the outlet channel 415 are less than fluid resistance of the inlet channel 413. Therefore, most of the liquid pushed out of the pressure chamber 44 due to rapid expansion of the piezoelectric element 45 is introduced into the ejection tube 50 through the outlet channel 415, and is ejected at a high speed as pulsed liquid droplets, that is, a pulsed liquid jet through the liquid ejection opening 61 having the diameter smaller than the diameter of the outlet channel.

The drive voltage increases to the maximum voltage, and then slowly decreases. At this time, the piezoelectric element 45 is contracted for a longer time than the rising time Tpr, and thus the diaphragm 46 is pulled to the piezoelectric element 45 so as to be bent toward the third case 43 side. If the diaphragm 46 is bent toward the third case 43 side and thus the volume of the pressure chamber 44 is increased, the liquid is introduced into the pressure chamber 44 from the inlet channel 413.

Since the liquid feeding pump device 20 supplies the liquid to the pulse flow generator 40 at predetermined pressure or a predetermined flow rate, if the piezoelectric element 45 does not perform an expansion operation, the liquid (steady flow) flowing in the pressure chamber 44 is introduced into the ejection tube 50 through the outlet channel 415, and is ejected from the liquid ejection opening 61. The ejected flow is a liquid flow at a constant and low speed, and may thus be regarded as a steady flow.

A description will be made of characteristic values of a flow velocity waveform of the main jet 3 with reference to FIG. 3B. Duration T of the main jet 3 is a period of time after a flow velocity waveform L13 returns to an initial flow velocity Ubg after increasing more than the flow velocity Ubg of a steady flow and reaching a peak. The duration T is a sum of a flow velocity rising time Tr required for a flow velocity to reach the peak and a flow velocity falling time Tf required for the flow velocity to return to the initial state from the peak. The maximum flow velocity Um of the main jet 3 is a sum of the flow velocity Ubg of the steady flow and the flow velocity maximum amplitude ΔUm.

Principle (First)

Fundamental values indicating features of a pulsed liquid jet are the driving voltage waveform L11 in FIG. 3A and the flow velocity waveform L13 of a jet corresponding to a single pulse in the liquid ejection opening 61. Above all, the main jet 3 which is a main peak portion (a jet in a head wave) at the maximum flow velocity generated right after rising of the drive voltage, extracted and illustrated in FIG. 3B, is focused. Other low peaks are caused by jets which are incidentally ejected since a pressure changing wave occurring in the pressure chamber 44 during expansion of the piezoelectric element 45 reflects and reciprocates in the ejection tube 50, but a cutting aspect such as a cut depth or a cut volume of the cutting target object is determined by the main jet 3 with the highest flow velocity.

In a case where a cut depth or a cut volume of the cutting target object is to be changed by changing the strength of a pulsed liquid jet, a drive voltage waveform for the piezoelectric element 45 is controlled. There may be a method of controlling the drive voltage waveform by the operator indicating a rising frequency of the drive voltage waveform or amplitude (voltage amplitude) of the drive voltage waveform as a voltage characteristic value. For example, there may be a method in which the operator indicates the rising frequency (or the rising time Tpr) in a state in which the voltage amplitude is fixed, or indicates the voltage amplitude in a state in which the rising frequency is fixed. This is because the voltage amplitude or the rising frequency (rising time Tpr) greatly influences a flow velocity waveform of the main jet 3. A drive voltage which is slowly decreasing after increasing to the maximum voltage does not greatly influence the flow velocity waveform of the main jet 3. Thus, if the rising frequency is heightened, or the voltage amplitude is increased, a cut depth and a cut volume are increased in proportion thereto. The voltage amplitude is the maximum value of the driving voltage waveform L11.

However, it has been proven that an actually obtained cut depth or cut volume of a cutting target object may not necessarily be changed in accordance with a change in the voltage characteristic value, and thus convenience may deteriorate. For example, there is a case where the operator increases the voltage amplitude to twice, but a cut depth or a cut volume may not be increased as expected, or decreases the voltage amplitude to a half, but a cut depth or a cut volume may not be reduced as expected. Thus, a situation may occur in which a cut depth or a cut volume desired by the operator is not obtained. This causes a problem of increasing surgery time.

There is a case where a cutting speed may be desired to be adjusted separately from the strength of a pulsed liquid jet. For this, there may be a method in which the operator indicates a repetition frequency of the drive voltage waveform. For example, heightening of the repetition frequency indicates increasing the number of times of ejection of a pulsed liquid jet per unit time, and, as a result, an obtained cut depth or cut volume is changed.

However, if the repetition frequency is changed, the drive voltage waveform is changed. As a result, even if the repetition frequency is changed, there is a case where a cut depth or a cut volume per unit time may not be changed in proportion thereto, and thus the operator's convenience may deteriorate. Specifically, there may be a method of changing the repetition frequency, for example, simply by enlarging and reducing the entire drive voltage waveform in a time axis direction. However, in this method, since a rising frequency which greatly influences a flow velocity waveform of the main jet 3 is varied, the strength of a pulsed liquid jet is changed as described above. As a result, a cutting speed as intended, proportional to a repetition frequency, cannot be obtained.

Therefore, focusing on a flow velocity waveform of the main jet 3, correlations of a cut depth and a cut volume with several parameters determined by the flow velocity waveform of the main jet 3 were examined. This is because, if a parameter highly correlated with a cut depth or a cut volume is found, the piezoelectric element 45 can be controlled with a drive voltage waveform which is optimal for achieving a cut depth or a cut volume corresponding to the user's operation sense.

For this, first, on the basis of a flow velocity waveform v [m/s] of the main jet 3 in the liquid ejection opening 61, mass flux [kg/s], momentum flux [N], and energy flux [W] of the main jet 3 passing through the liquid ejection opening 61, were examined. The mass flux is mass [kg/s] per unit time of a liquid passing through the liquid ejection opening 61. The momentum flux is momentum [N] per unit time of a liquid passing through the liquid ejection opening 61. The energy flux is energy [W] per unit time of a liquid passing through the liquid ejection opening 61. The energy indicates kinetic energy, and will be hereinafter abbreviated to "energy".

In the liquid ejection opening 61, a liquid is released to a free space, and thus pressure may be regarded to be "0". A velocity of the liquid in a direction orthogonal to a jet ejection direction (a diameter direction of the liquid ejection opening 61) may also be regarded to be "0". Assuming that there is no velocity distribution of a liquid in a diameter direction of the liquid ejection opening 61, mass flux Jm [kg/s], momentum flux Jp [N], and energy flux Je [W] of the liquid passing through the liquid ejection opening 61 may be respectively obtained according to the following Equations (1), (2) and (3). S [m$^2$] indicates a nozzle sectional area, and ρ [kg/m$^3$] indicates a working fluid density.

$$Jm = S \cdot p \cdot v \quad (1)$$

$$Jp = S \cdot p \cdot v^2 \quad (2)$$

$$Je = 1/2 \cdot p \cdot S \cdot v^3 \quad (3)$$

Figure 4A:
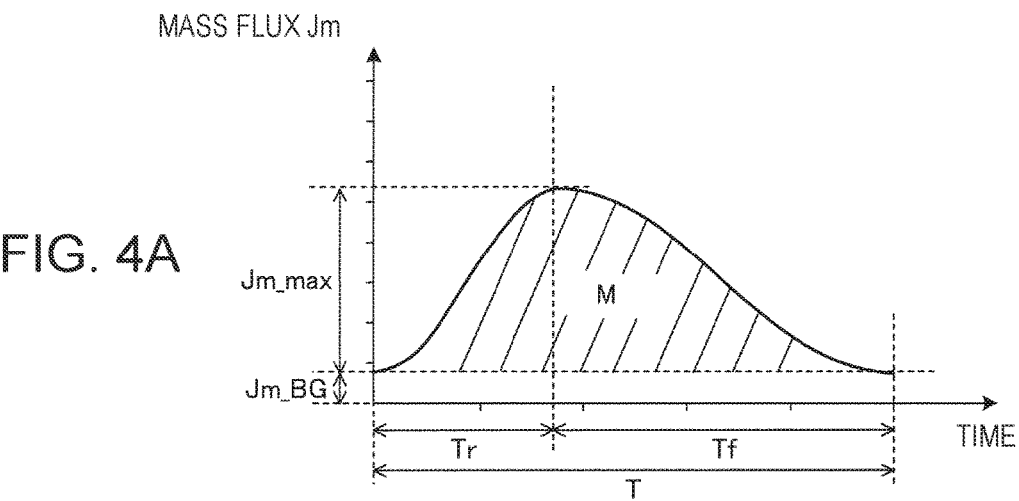
FIGS. 4A to 4C are diagrams respectively illustrating mass flux, momentum flux, and energy flux.
Figure 4B:
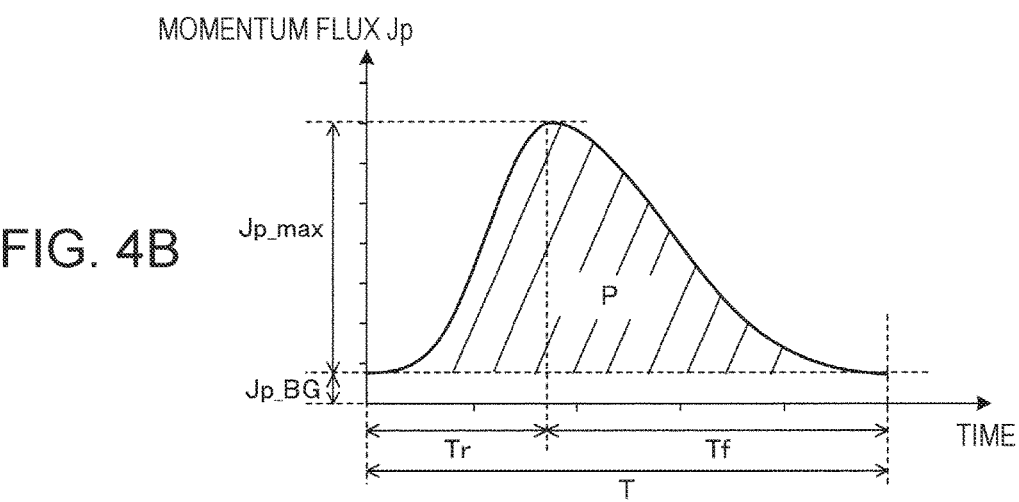
Figure 4C:
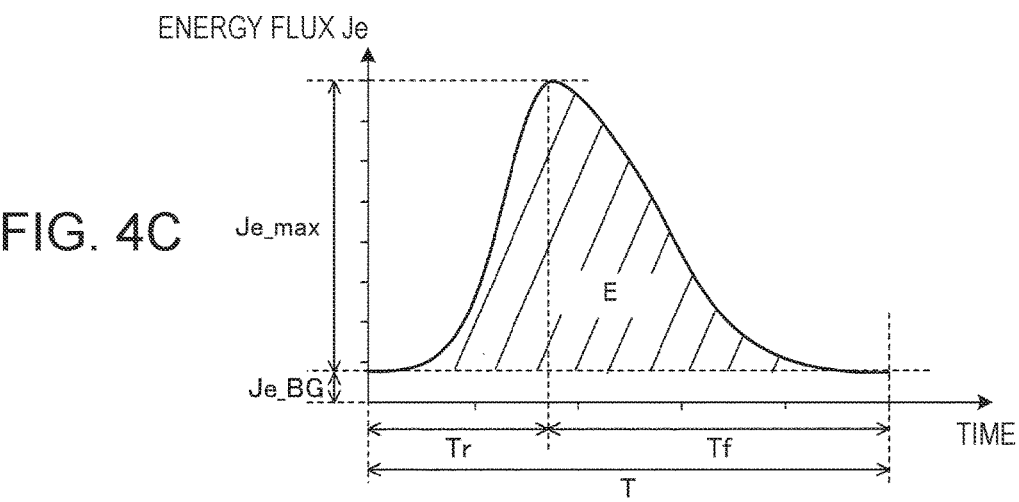

FIGS. 4A to 4C are diagrams respectively illustrating mass flux Jm (FIG. 4A), momentum flux Jp (FIG. 4B), and energy flux Je (FIG. 4C) obtained on the basis of the flow velocity waveform of the main jet 3 illustrated in FIG. 3B. If each of the mass flux Jm, the momentum flux Jp, and the energy flux Je is integrated over time (duration) T from rising to falling of the flow velocity waveform of the main jet 3, mass, momentum, and energy of a liquid ejected from the liquid ejection opening 61 as the main jet 3 can be obtained.

The values of the mass flux Jm, the momentum flux Jp, the energy flux Je, the mass, the momentum, and the energy calculated in the above-described way may determine a cut depth and a cut volume related to the main jet 3 corresponding to a single pulse. However, each of the above values is a physical quantity including a quantity corresponding to a steady flow, and it is noted that a value thereof is obtained by subtracting an attribution of the steady flow.

Therefore, regarding the mass flux Jm illustrated in FIG. 4A, two parameters are defined, such as the maximum mass flux Jm_max [kg/s] obtained by subtracting mass flux Jm_BG [kg/s] of a steady flow from a peak value (maximum value) of the mass flux Jm, and outflow mass M [kg], hatched in FIG. 4A, obtained by excluding an amount corresponding to the steady flow from mass of a liquid flowing out of the liquid ejection opening 61 as the main jet 3. The outflow mass M is expressed by the following Equation (4).

$$M = \int (Jm - Jm\_BG) dt \quad (4)$$

Regarding the momentum flux Jp illustrated in FIG. 4B, two parameters are defined, such as the maximum momentum flux Jp_max [N] obtained by subtracting momentum flux Jp_BG [N] of a steady flow from a peak value (maximum value) of the momentum flux Jp, and momentum P [Ns], hatched in FIG. 4B, obtained by excluding an amount corresponding to the steady flow from momentum of a liquid flowing out of the liquid ejection opening 61 as the main jet 3. The momentum P is expressed by the following Equation (5).

$$P = \int (Jp - Jp\_BG) dt \quad (5)$$

Regarding the energy flux Je illustrated in FIG. 4C, two parameters are defined, such as the maximum energy flux Je_max [W] obtained by subtracting energy flux Je_BG [W] of a steady flow from a peak value (maximum value) of the energy flux Je, and energy E [J], hatched in FIG. 4C, obtained by excluding an amount corresponding to the steady flow from energy of a liquid flowing out of the liquid ejection opening 61 as the main jet 3. The energy E is expressed by the following Equation (6).

$$E = \int (Je - Je\_BG) dt \quad (6)$$

Here, the integration section in each of the above Equations (4), (5) and (6) is time (duration) T from rising to falling of the main jet 3 in the flow velocity waveform.

By using numerical value simulation, to what extent each of the six parameters such as the maximum mass flux Jm_max, the outflow mass M, the maximum momentum flux Jp_max, the momentum P, the maximum energy flux Je_max, and the energy E is correlated with a cut depth and a cut volume was examined.

Here, a pulsed liquid jet is a fluid, and a cutting target object is a soft elastic body. Therefore, in order to perform simulation for a destruction behavior of the cutting target object using the pulsed liquid jet, an appropriate destruction threshold value is set on the soft elastic body side, and then so-called interaction analysis (fluid structure interaction (FSI) analysis) of the fluid and a structure (here, the soft elastic body) is required to be performed. Embodiments of computation methods in simulation may include a finite element method (FEM), a method using a particle method whose representative is a smoothed particle hydrodynamics (SPH), and a method of combining the finite element method with the particle method. An applied method is not particularly limited. Thus, although not described in detail, an optimal method was selected by taking into consideration of stability of an analysis result, computation time, and the like, and the simulation was performed.

When the simulation was performed, a fluid density=1 g/cm$^3$, a diameter of the liquid ejection opening 61=0.15 mm, and a standoff distance (a distance from the liquid ejection opening 61 to a surface of the cutting target object)=0.5 mm were set. Assuming that the cutting target object was a soft elastic body having a flat surface, a Mooney-Rivlin super-elastic body having a density of 1 g/cm$^3$ and an elastic modulus of about 9 kPa (about 3 kPa in terms of shear modulus) in terms of Young's modulus was used as a physical model thereof. Equivalent deviation strain=0.7 was used in the destruction threshold value.

Regarding flow velocity waveforms of the main jet 3, various flow velocity waveforms were assumed, and a total of flow velocity waveforms of 27 types were prepared by changing amplitude (the maximum value of flow velocity) of three types in a range of 12 m/s to 76 m/s and changing duration of three type in a range of 63 µs to 200 µs, with respect to each of waveforms of three types such as a sine wave, a triangular wave, and a rectangular wave. A flow velocity of a steady flow was 1 m/s.

Figure 5A:
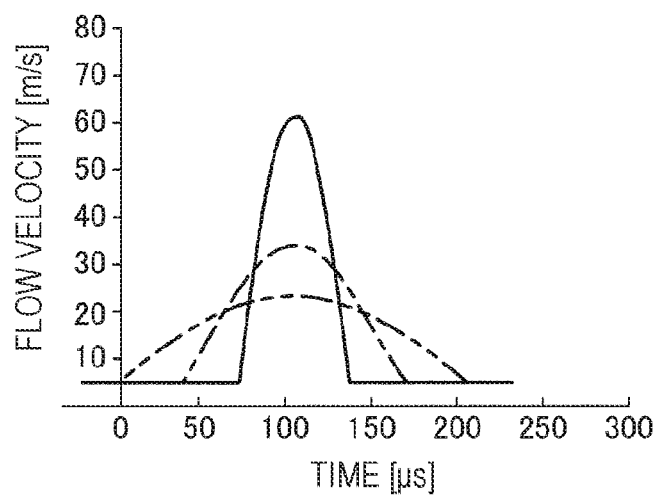
FIGS. 5A to 5C are diagrams illustrating flow velocity waveforms of a main jet used in simulation for a cutting aspect of a cutting target object.
Figure 5B:
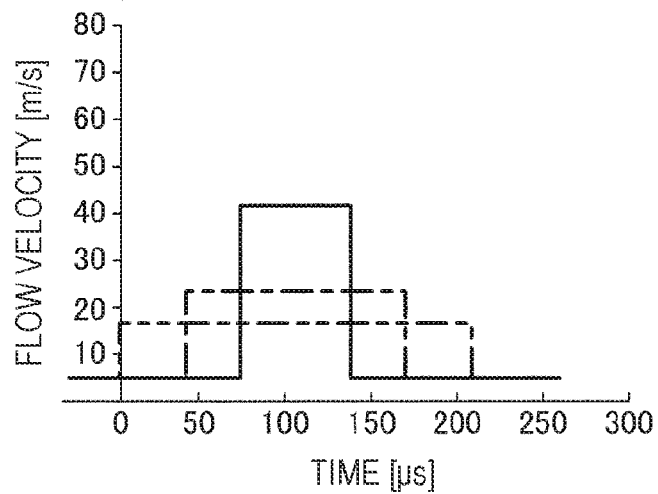
Figure 5C:
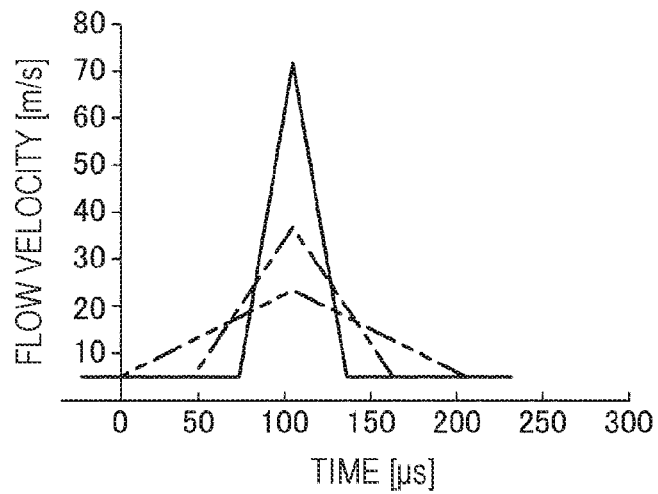

FIGS. 5A to 5C respectively illustrate a sine wave (FIG. 5A), a rectangular wave (FIG. 5B), and a triangular wave (FIG. 5C) provided as flow velocity waveforms of the main jet 3 in the simulation, in which a solid line indicates a case where the duration is 63 µs, a dot chain line indicates a case where the duration is 125 µs, and a two-dot chain line indicates a case where the duration is 200 µs. The prepared waveforms were provided as flow velocity waveforms of the main jet 3 so that pulsed liquid jets were generated, the simulation for a destruction behavior of the soft elastic body when the pulsed liquid jets were ejected onto the soft elastic body was performed, and a cut depth or a cut volume was examined.

FIGS. 6A to 6F are diagrams respectively plotting simulation results in a case where a longitudinal axis expresses a cut depth of a cutting target object, and a transverse axis expresses the maximum mass flux Jm_max (FIG. 6A), the outflow mass M (FIG. 6B), the maximum momentum flux Jp_max (FIG. 6C), the momentum P (FIG. 6D), the maximum energy flux Je_max (FIG. 6E), and the energy E (FIG. 6F). In FIGS. 6A to 6F, a simulation result obtained when a sine wave with the duration of 63 µs is provided as a flow velocity waveform of the main jet 3 is indicated by a plot of "*"; a simulation result obtained when a sine wave with the duration of 125 µs is provided as a flow velocity waveform of the main jet is indicated by a plot of "♦"; and a simulation result obtained when a sine wave with the duration of 200 µs is provided as a flow velocity waveform of the main jet is indicated by a plot of "–". In addition, a simulation result obtained when a triangular wave with the duration of 63 µs is provided as a flow velocity waveform of the main jet 3 is indicated by a plot of "+"; a simulation result obtained when a triangular wave with the duration of 125 µs is provided as a flow velocity waveform of the main jet is indicated by a plot of "X"; and a simulation result obtained when a triangular wave with the duration of 200 µs is provided as a flow velocity waveform of the main jet is indicated by a plot of a square shape displayed black. Further, a simulation result obtained when a rectangular wave with the duration of 63 µs is provided as a flow velocity waveform of the main jet 3 is indicated by a plot of "●"; a simulation result obtained when a rectangular wave with the duration of 125 µs is provided as a flow velocity waveform of the main jet is indicated by a plot of a triangular shape displayed black; and a simulation result obtained when a rectangular wave with the duration of 200 µs is provided as a flow velocity waveform of the main jet is indicated by a plot of "—".

As illustrated in FIGS. 6A, 6C and 6E, the relationship between each of the three parameters such as the maximum mass flux Jm_max, the maximum momentum flux Jp_max, and the maximum energy flux Je_max, and the cut depth greatly varies depending on the shape of the waveform provided as a flow velocity waveform of the main jet 3, and thus it was found that a mutual correlation is low. Especially, this suggests that the mass flux has a value proportional to a flow velocity, and thus a cut depth is not defined by only the maximum flow velocity of the main jet 3.

Next, regarding the relationship between each of the three parameters such as the outflow mass M, the momentum P, and the energy E, illustrated in FIGS. 6B, 6D and 6F, and the cut depth, the relationship between the outflow mass M and the cut depth greatly varies depending on the shape of the waveform provided as a flow velocity waveform of the main jet 3, and thus a mutual correlation is low. In contrast, in the relationship with the momentum P or the energy E, a variation due to the shape of the provided waveform is small, and the respective plots are substantially distributed on the same curve. Of the momentum P and the energy E, the momentum P less varies. Therefore, it can be said that the cut depth has a high correlation with the momentum P or the energy E, and is highly correlated with, especially, the momentum P.

Here, the simulation was performed in a case where the diameter of the liquid ejection opening was 0.15 mm, and a standoff distance was 0.5 mm, but simulation was performed for other liquid ejection opening diameters or standoff distances, and it was found that a quantitative tendency that the cut depth is highly correlated with the momentum P or the energy E does not greatly change.

Figure 7E:
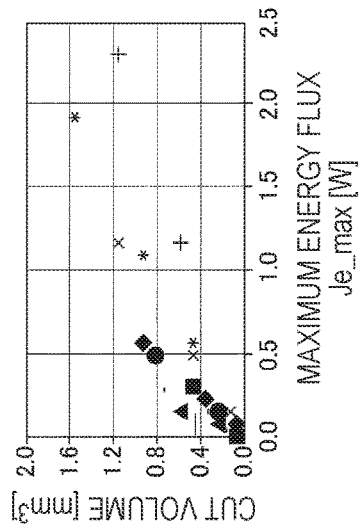
FIGS. 7A to 7F are diagrams illustrating simulation results (cut volumes).
Figure 7C:
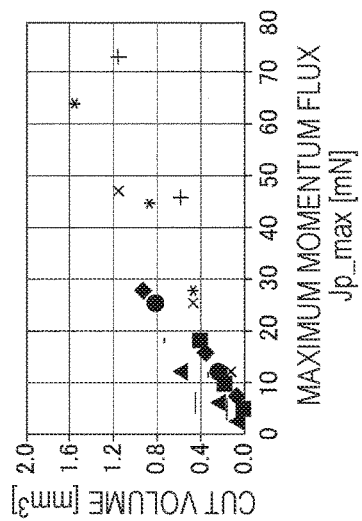
Figure 7A:
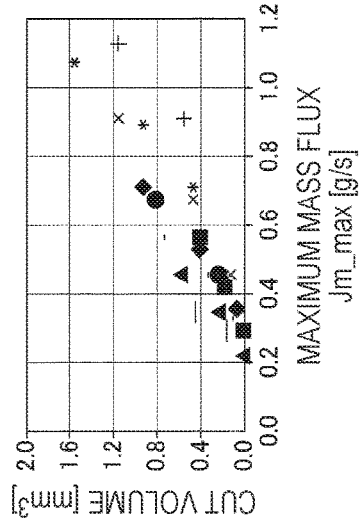
Figure 7F:
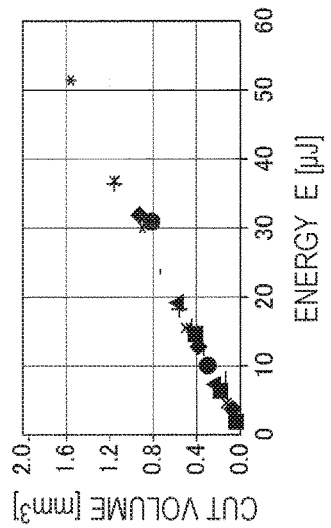

FIGS. 7A to 7F are diagrams respectively plotting simulation results in a case where a longitudinal axis expresses a cut volume of a cutting target object, and a transverse axis expresses the maximum mass flux Jm_max (FIG. 7A), the outflow mass M (FIG. 7B), the maximum momentum flux Jp_max (FIG. 7C), the momentum P (FIG. 7D), the maximum energy flux Je_max (FIG. 7E), and the energy E (FIG. 7F). Relationships between waveforms provided as a flow velocity waveform of the main jet 3 and the types of plots are the same as in FIGS. 6A to 6F.

As illustrated in FIGS. 7A, 7C and 7E, the relationship between each of the three parameters such as the maximum mass flux Jm_max, the maximum momentum flux Jp_max, and the maximum energy flux Je_max, and the cut volume varies depending on the shape of the waveform provided as a flow velocity waveform of the main jet 3 although not as much as the relationship with the cut depth, and thus it is considered that a mutual correlation is low.

Figure 7D:
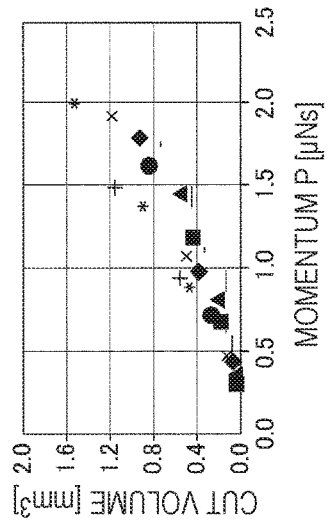
Figure 7B:
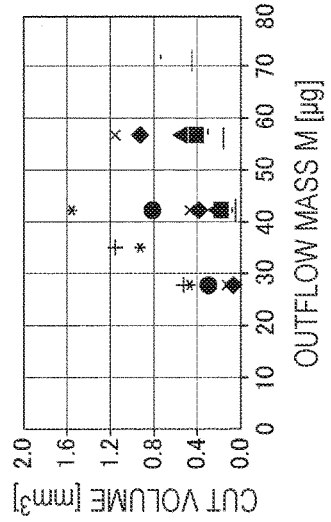

Next, regarding the relationship between each of the three parameters such as the outflow mass M, the momentum P, and the energy E, illustrated in FIGS. 7B, 7D and 7F, and the cut volume, the relationship between the outflow mass M and the cut volume greatly varies depending on the shape of the waveform provided as a flow velocity waveform of the main jet 3 in the same manner as in the cut depth, and thus a mutual correlation is low. In contrast, in the relationship with the momentum P or the energy E, a variation due to the shape of the provided waveform is small in the same manner as in the cut depth, and the respective plots are substantially distributed on the same straight line. The energy E less varies than the momentum P. Therefore, it can be said that the cut volume has a high correlation with the momentum P or the energy E, and is highly correlated with, especially, the energy E.

Here, the simulation was performed in a case where the diameter of the liquid ejection opening was 0.15 mm, and a standoff distance was 0.5 mm, but simulation was performed for other liquid ejection opening diameters or standoff distances, and it was found that a quantitative tendency that the cut volume is highly correlated with the momentum P or the energy E does not greatly change.

In the present embodiment, the energy E is focused on the basis of the above examination results. Simulation for representative drive voltage waveforms which are actually applied to the piezoelectric element 45 is performed in advance, and thus correspondence relationships between the energy E and control parameters defining the drive voltage waveforms are acquired.

In "Principle (first)", there may be various control parameters, but, here, three control parameters such as a rising frequency, voltage amplitude, and a repetition frequency are used. A flow velocity waveform of the main jet 3 was obtained through simulation by setting the control parameters to be variable. The simulation may be performed, for example, by using numerical value simulation which is based on a model replacing a channel system of the liquid ejection device with fluid (channel) resistance, fluid inertance, fluid compliance, or the like, and which uses an equivalent circuit method. Alternatively, if higher accuracy is required, fluid simulation using a finite element method (FEM), a finite volume method (FVM), or the like may be used.

Figure 8A:
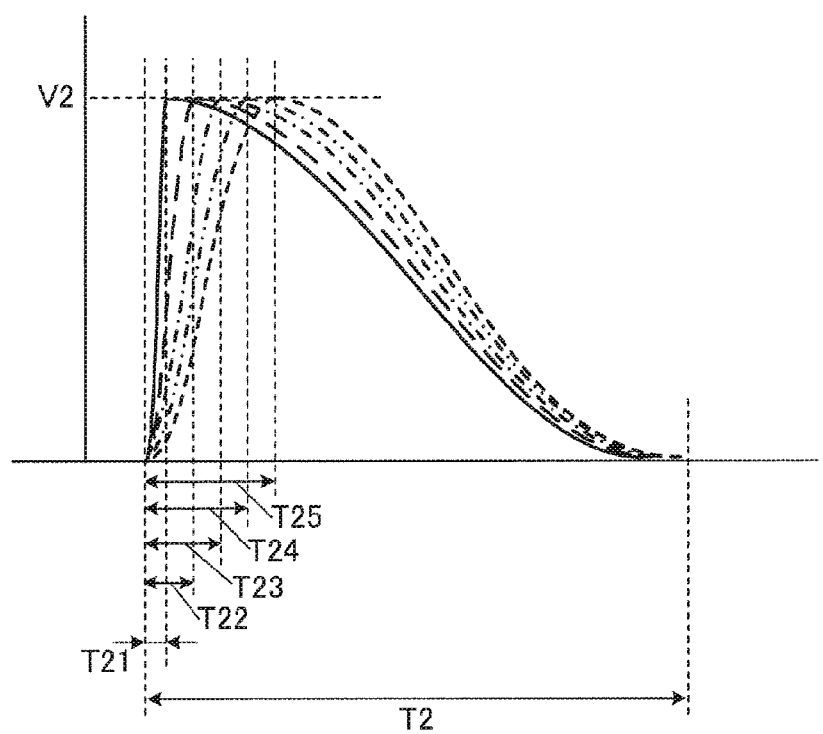
FIGS. 8A and 8B are diagrams illustrating simulation results of flow velocity waveforms of a main jet in a case where drive voltage waveforms with different rising frequencies are applied.

First, the flow velocity waveform of the main jet 3 is obtained through simulation by providing a drive voltage waveform in which the rising frequency is changed in steps in a state in which the voltage amplitude and the repetition frequency are fixed. FIG. 8A is a diagram illustrating examples of the provided drive voltage waveforms. In each drive voltage waveform, the voltage amplitude is V2, the repetition cycle Tp is T2, and the rising time Tpr is lengthened in steps from T21 to T25 (the rising frequency is lowered in steps).

Figure 8B:
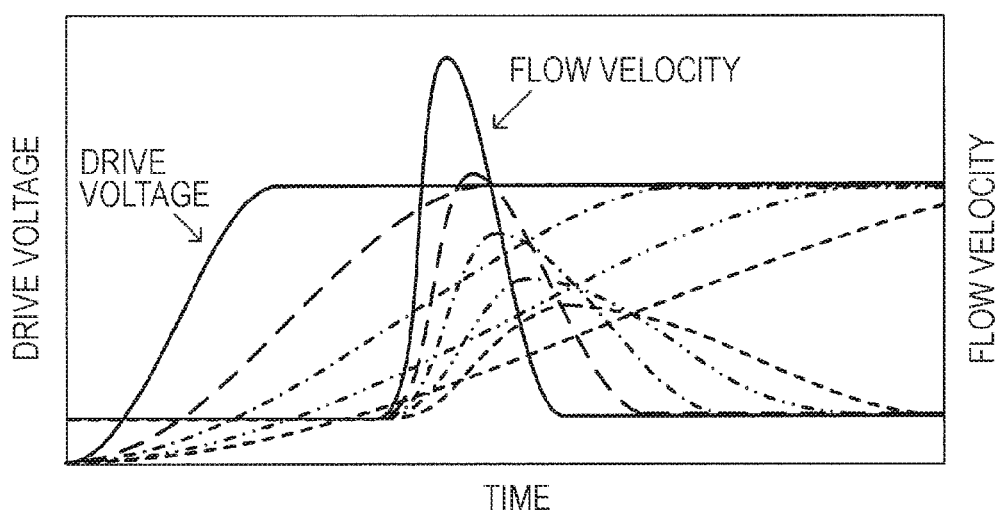

FIG. 8B is a diagram illustrating simulation results of the flow velocity waveform of the main jet 3 in a case where drive voltage waveforms with the different rising frequencies illustrated in FIG. 8A are provided. As illustrated in FIG. 8B, if the rising frequency is low (the rising time Tpr is long), in the flow velocity waveform of the main jet 3, a rising start timing does not vary, and the duration during rising is lengthened, and thus flow velocity amplitude (the maximum value of the flow velocity) is also reduced.

Figure 9A:
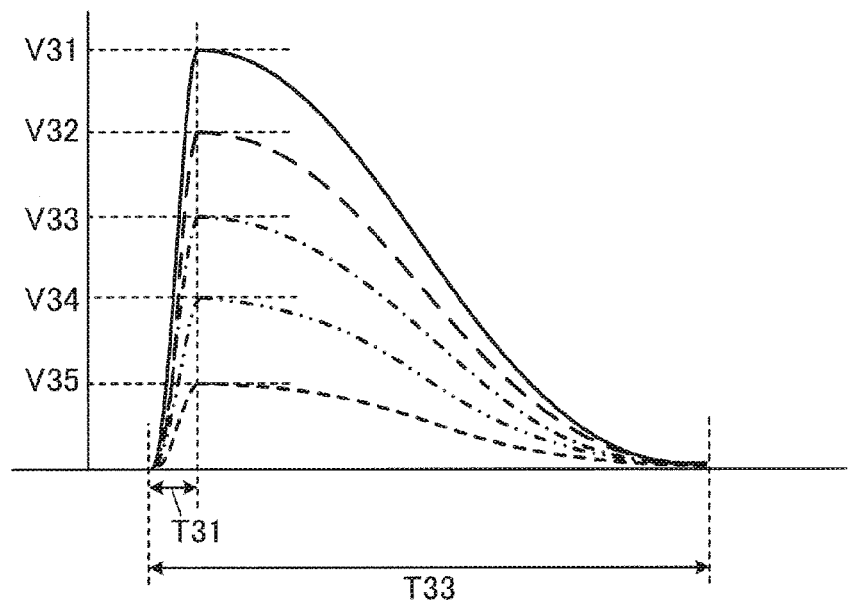
FIGS. 9A and 9B are diagrams illustrating simulation results of flow velocity waveforms of a main jet in a case where drive voltage waveforms with different voltage amplitudes are applied.

Second, the flow velocity waveform of the main jet 3 is obtained through simulation by providing a drive voltage waveform in which the voltage amplitude is changed in steps in a state in which the rising frequency and the repetition frequency are fixed. FIG. 9A is a diagram illustrating examples of the provided drive voltage waveforms. In each drive voltage waveform, the rising time Tpr is T31, the repetition cycle Tp is T33, and the voltage amplitude is reduced in steps from V31 to V35.

Figure 9B:
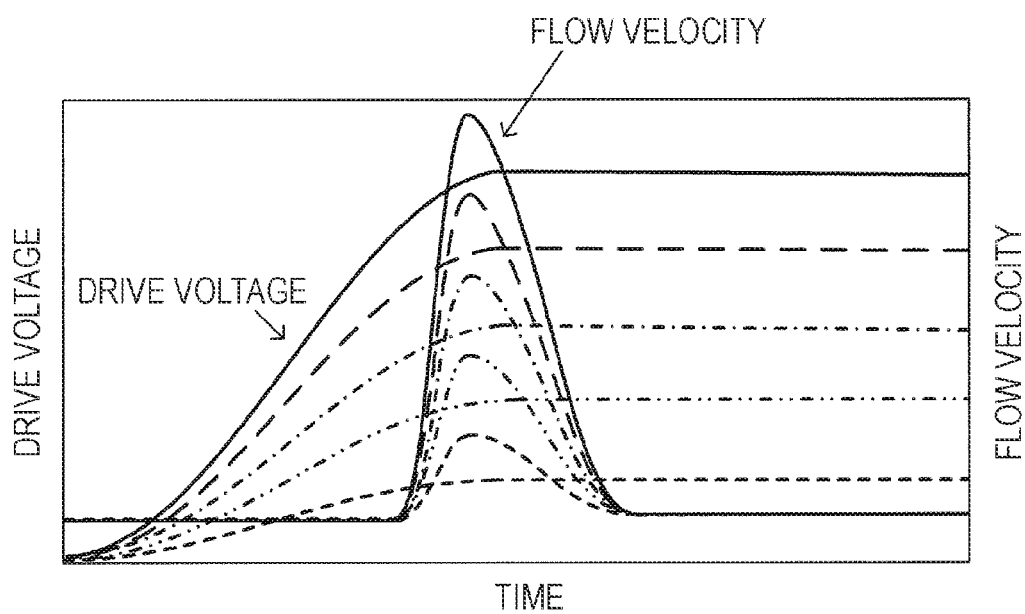

FIG. 9B is a diagram illustrating simulation results of the flow velocity waveform of the main jet 3 in a case where drive voltage waveforms with the different voltage amplitudes illustrated in FIG. 9A are provided. As illustrated in FIG. 9B, if the voltage amplitude is reduced, in the flow velocity waveform of the main jet 3, the duration during rising is maintained unlike in the cases where the rising frequency is reduced, and flow velocity amplitude (the maximum value of the flow velocity) is reduced.

Figure 10A:
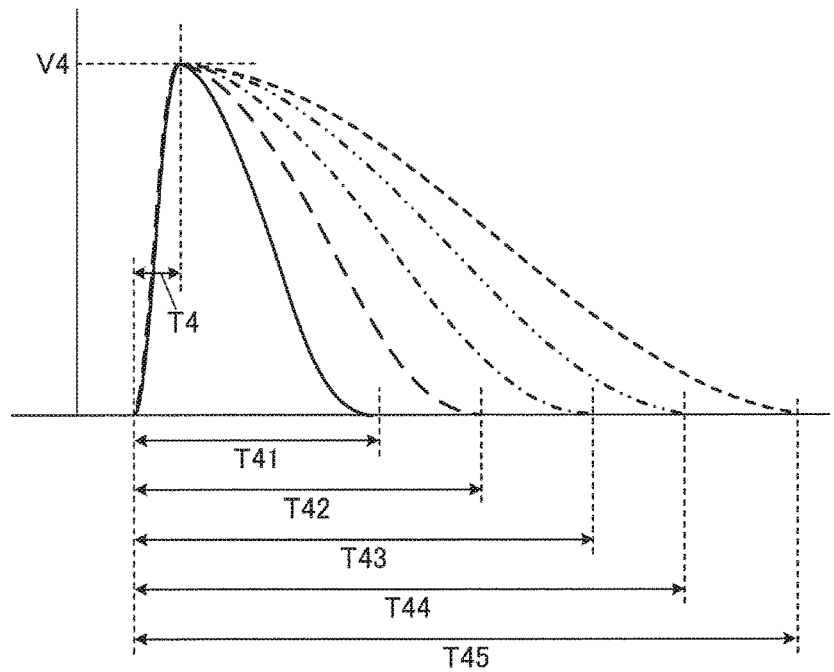
FIGS. 10A and 10B are diagrams illustrating simulation results of flow velocity waveforms of a main jet in a case where drive voltage waveforms with different repetition frequencies are applied.

Third, the flow velocity waveform of the main jet 3 is obtained through simulation by providing a drive voltage waveform in which the repetition frequency is changed insteps in a state in which the rising frequency and the voltage amplitude are fixed. FIG. 10A is a diagram illustrating examples of the provided drive voltage waveforms. In each drive voltage waveform, the rising time Tpr is T4, the voltage amplitude is V4, and the repetition cycle Tp is lengthened in steps from T41 to T45 by extending, in a time axis direction, a falling shape after a drive voltage increases up to the maximum voltage (the repetition frequency is lowered in steps).

Figure 10B:
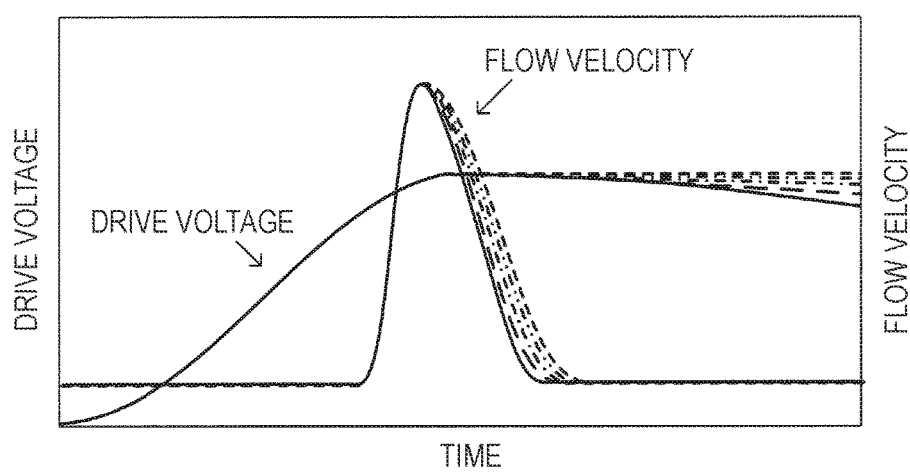

FIG. 10B is a diagram illustrating simulation results of the flow velocity waveform of the main jet 3 in a case where drive voltage waveforms with the different repetition frequencies illustrated in FIG. 10A are provided. As illustrated in FIG. 10B, if the repetition frequency is lowered (the repetition cycle Tp is lengthened), in the flow velocity waveform of the main jet 3, the duration is slightly lengthened compared with the cases where the rising frequency is reduced. The flow velocity amplitude (the maximum value of the flow velocity) is maintained to be constant.

Next, the energy E is obtained for each of the obtained flow velocity waveforms of the main jet 3.

Specifically, for each repetition frequency while changing the repetition frequency in the way described with reference to FIGS. 10A and 10B, simulation is performed in a case where the voltage amplitude is fixed and the rising frequency is changed in the way described with reference to FIGS. 8A and 8B and simulation is performed in a case where the rising frequency is fixed and the voltage amplitude is changed in the way described with reference to FIGS. 9A and 9B. The energy E of the flow velocity waveform of the main jet 3 obtained through each simulation is obtained.

Figure 11:
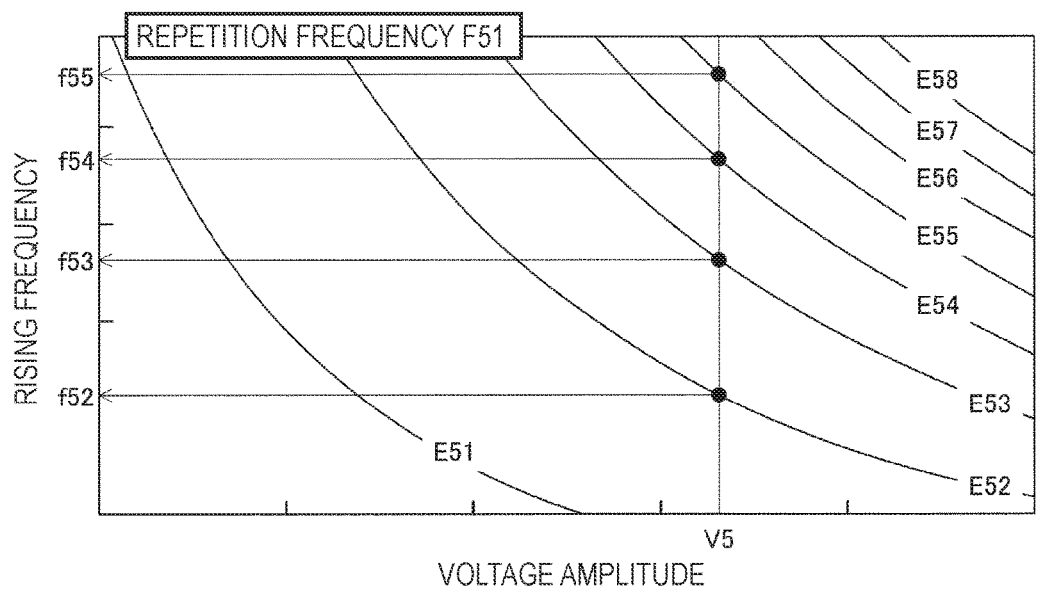
FIG. 11 is a diagram illustrating a correspondence relationship among energy, a rising frequency, and voltage amplitude at a predetermined repetition frequency.

FIG. 11 is a diagram illustrating correspondence relationships among the energy E obtained at a predetermined repetition frequency (for example, "F51"), the rising frequency, and the voltage amplitude. FIG. 11 is obtained by drawing contour lines regarding the energy E in a coordinate space in which a longitudinal axis expresses the rising frequency, and a transverse axis expresses the voltage amplitude. Energies E51, E52, . . . of the respective contour lines are low on the lower left side in FIG. 11, and increase by a predetermined amount toward the upper right side. Although not illustrated, if contour lines are drawn by plotting the energy E obtained at another repetition frequency in the same coordinate space, a contour map corresponding to correspondence relationships among the energy E at the repetition frequency, the rising frequency, and the voltage amplitude is obtained.

Here, it is noted that the energy E does not linearly change for the parameter in each coordinate axis direction. For example, in the correspondence relationships among the energy E, the rising frequency, and the voltage amplitude illustrated in FIG. 11, a case is assumed that the voltage amplitude is fixed (to V5, for example), a drive voltage waveform for the piezoelectric element 45 is controlled by changing the rising frequency. In a case where an amount of the energy E to be changed is to be constant, a rising frequency change between the rising frequencies f52 and f53 is necessary between the energies E52 and E53, and a rising frequency change between the rising frequencies f53 and f54 is necessary between the energies E53 and E54. However, a rising frequency gap between the rising frequencies f52 and f53 is different from a rising frequency gap between the rising frequencies f53 and f54. This phenomenon notably appears as the energy E increases. Therefore, in a case where an operation of changing the rising frequency by a predetermined amount in a state in which the voltage amplitude is fixed, the energy E does not changed as expected, and thus it can be said that a situation may occur in which a cut depth or a cut volume is not changed as intended or perceived by an operator. This may also be same for a case where an operation of changing the voltage amplitude by a predetermined amount in a state in which the rising frequency is fixed.

Principle (Second)

Next, an additional control parameter is introduced in addition to the above-described three control parameters defining a drive voltage waveform. The control parameter is a parameter called a waveform shape (hereinafter, referred to as a "rising waveform shape") related to rising of the drive voltage waveform.

Figure 12:
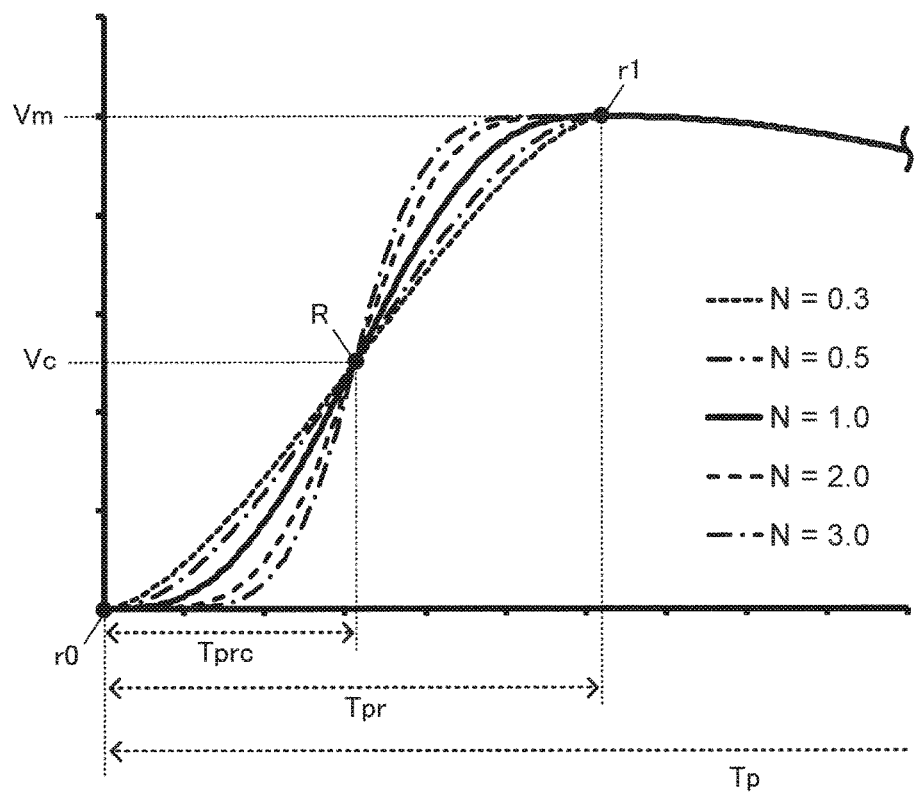
FIG. 12 is an enlarged view of a rising portion of a drive voltage waveform.

FIG. 12 is an enlarged view of the rising portion of the drive voltage waveform.

Focusing on the rising portion in relation to an inflection point R of a waveform curve, it can be seen that the rising portion is formed of two curve portions such as a portion which increases along a curve projecting downwardly from the drive voltage of "0" and reaches the inflection point R and a portion which reaches the voltage amplitude Vm along a curve projecting upwardly from the inflection point R. The piezoelectric element 45 is substantially linearly expanded for the drive voltage V, and thus it can be said that the inflection point R corresponds to a peak of the flow velocity waveform L13 of the main jet 3. Therefore, a waveform shape (hereinafter, referred to as a "rising first-half waveform shape") reaching the inflection point R from the drive voltage of "0" and a waveform shape (hereinafter, referred to as a "rising second-half waveform shape") reaching the voltage amplitude Vm from the inflection point Rare adjusted, and thus a flow velocity waveform of the main jet 3 can be changed without changing a flow velocity peak timing.

Specifically, in order to verify the effect achieved by changing a rising waveform shape, the three control parameters such as the voltage amplitude, the repetition frequency, and the rising frequency are fixed. In other words, a rising waveform shape is changed by changing a tendency for a voltage to increase, for example, by causing the voltage to slowly start or rapidly start in a state in which positions in the drive voltage waveform of a "rising start point r0 (a point of the drive voltage=0)", a "rising end point r1 (the drive voltage=voltage amplitude)", and the inflection point R (a timing and a drive voltage) are fixed.

A change ratio of a voltage between the start point r0 and the end point r1 can be said to be higher in a case of "rapid starting" than in a case of "slow starting". A change ratio of a voltage around the inflection point R can be said to be higher in a case of "rapid starting" than in a case of "slow starting". A slope of a drive voltage waveform around the inflection point is closer to 90° in a case of "rapid starting" than in a case of "slow starting".

For example, it is assumed that the inflection point R is located at an intersection between a drive voltage waveform and a line segment connecting the rising start point r0 and the rising end point r1 of the drive voltage waveform. FIG. 12 illustrates a correspondence relationship between a value of N and a rising waveform shape in a reference waveform. V(t) with N as a variable, as an example. The waveform shape is defined according to Equation (7) which will be described later. In FIG. 12, if a rising waveform shape is gradually close to a linear shape so as to be close to a waveform of N=0.3 from a waveform of N=3.0, a flow velocity waveform of the main jet 3 becomes a more slowly increasing waveform. On the other hand, in FIG. 12, if a rising waveform shape is gradually close to a waveform (for example, a waveform having a stepwise shape) in which a drive voltage rapidly increases at the inflection point R so as to be close to the waveform of N=3.0 from the waveform of N=0.3, a flow velocity waveform of the main jet 3 becomes a flow velocity waveform in which a flow velocity more rapidly increases at a timing corresponding to the inflection point R.

Figure 13:
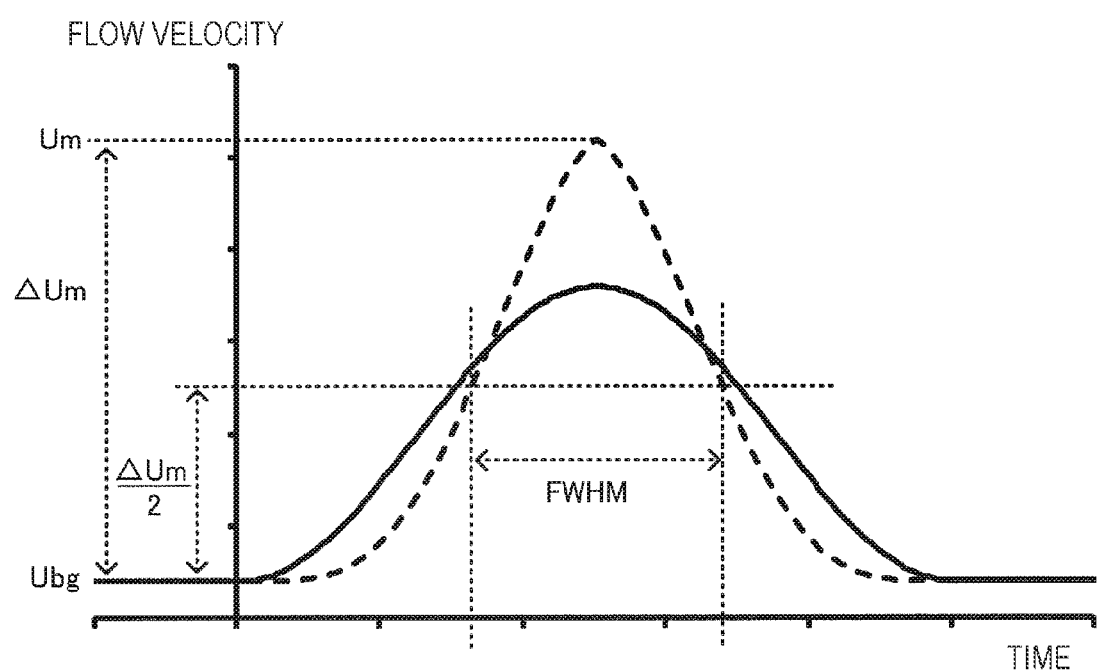
FIG. 13 is a diagram illustrating a change of a flow velocity waveform of a main jet for a change of a rising waveform shape.

FIG. 13 schematically illustrates a change of a flow velocity waveform of the main jet 3 for a change of a rising waveform shape. FIG. 13 shows two flow velocity waveforms, in which a solid line flow velocity waveform indicates a case where an increasing tendency of the rising waveform shape is slow, and a dashed line flow velocity waveform indicates a case where an increasing tendency of the rising waveform shape is rapid. The outflow masses M (refer to FIG. 4A) are the same as each other, and flow velocity peak timings are also the same as each other in both of the cases. However, the maximum flow velocities Um are different from each other, and the entire shapes of the flow velocity waveforms are also different from each other. Therefore, a full width at half maximum is employed as a value indicating characteristics of the flow velocity waveform. FIG. 13 illustrates respective variables for calculation of a full width at half maximum FWHM for the dashed line flow velocity waveform. The full width at half maximum FWHM for the dashed line flow velocity waveform is a period of time from a time point at which the flow velocity reaches a value (hereinafter, referred to as a "half value") obtained by adding a half value ($\Delta$Um/2) of the flow velocity maximum amplitude $\Delta$Um to the flow velocity Ubg of the steady flow, during increasing, to a time point at which the flow velocity reaches a half value during decreasing.

A small full width at half maximum FWHM indicates that a flow velocity waveform entirely has a steep shape, and a large full width at half maximum FWHM indicates that a flow velocity waveform entirely has a gentle shape.

Next, simulation for a cut depth and a cut volume in a case of changing a full width at half maximum FWHM of a flow velocity waveform was performed, and a result thereof will be described.

The simulation was performed according to the same computation method as the above-described simulation for a flow velocity waveform. In other words, a pulsed liquid jet is a fluid, and a cutting target object is a soft elastic body. Therefore, the simulation was performed as a destruction behavior of a cutting target object using a pulsed liquid jet. As a computation method in the simulation, in the present embodiment, an appropriate destruction threshold value is set on the soft elastic body side, and then so-called interaction analysis (fluid structure interaction (FSI) analysis) of the fluid and a structure (here, the soft elastic body) is employed, but a finite element method (FEM), a method using a particle method whose representative is a smoothed particle hydrodynamics (SPH), and a method of combining the finite element method with the particle method may be employed.

When the simulation was performed, a diameter of the liquid ejection opening 61=0.15 mm, and a standoff distance (a distance from the liquid ejection opening 61 to a surface of the cutting target object)=1.0 mm were set. Assuming that the cutting target object was a soft elastic body having a flat surface, a Mooney-Rivlin super-elastic body having an elastic modulus of about 9 kPa (about 3 kPa in terms of shear modulus) in terms of Young's modulus was used as a physical model thereof. Equivalent deviation strain=0.7 was used in the destruction threshold value. Both of the density of the liquid and the density of the soft elastic body were 1 g/cm$^3$.

Regarding the flow velocity waveform L13 of the main jet 3 which is forced to be applied to a nozzle hole outlet and is ejected onto a cutting target object, a flow velocity waveform in which the maximum flow velocity Um was 50 m/s, the duration T was 125 μs, and the full width at half maximum FWHM was 61 μs was used as a "reference flow velocity waveform", and the flow velocity waveforms L13 was assumed in which the duration T and the outflow mass M are fixed, and various full widths at half maximum FWHM are taken. Specifically, six levels such as 39 μs, 48 μs, 61 μs, 74 μs, 85 μs, and 124 μs were assumed as the full width at half maximum FWHM of the flow velocity waveform. The flow velocity Ubg of a steady flow was 1 m/s.

Figure 14A:
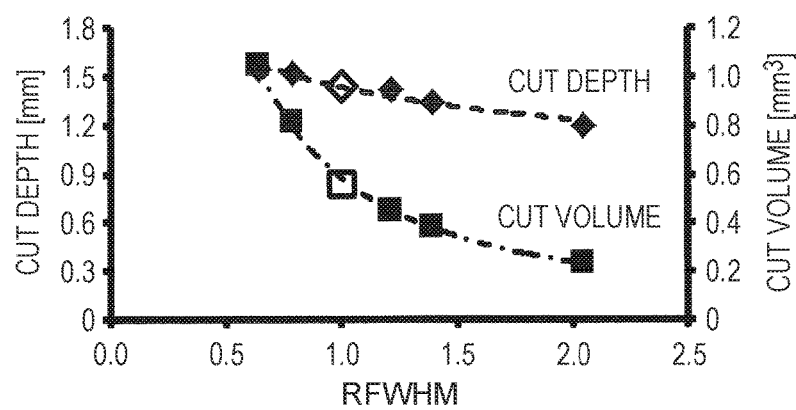
FIGS. 14A to 14C are diagrams illustrating simulation results of a cut depth and a cut volume in a case where a full width at half maximum of a flow velocity waveform is changed.
Figure 14B:
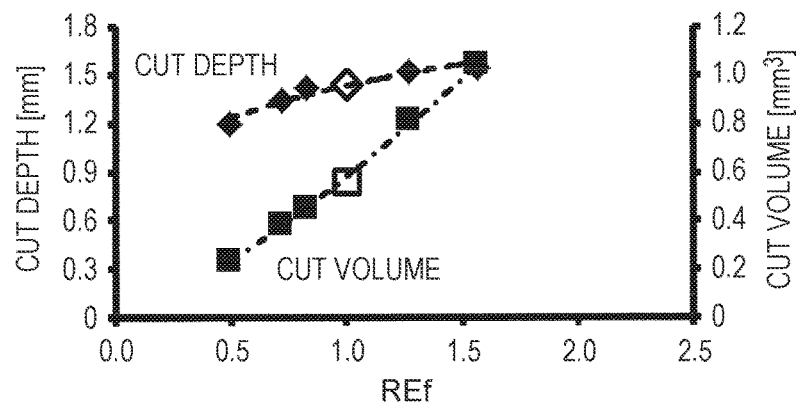
Figure 14C:
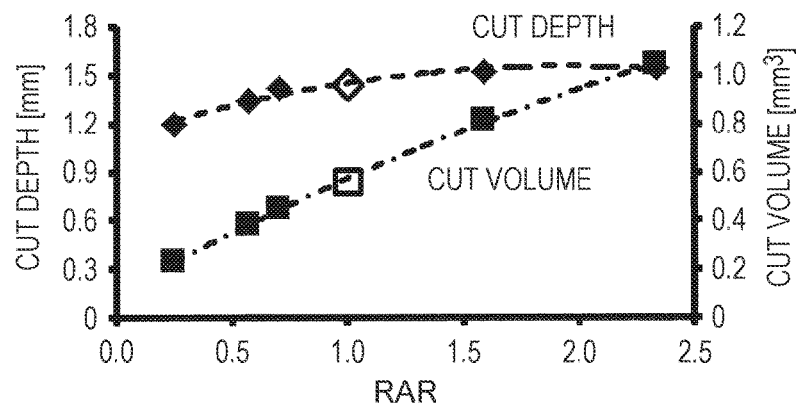

FIGS. 14A to 14C illustrate simulation results. In FIGS. 14A to 14C, transverse axes are different from each other, and the longitudinal axes are the same as each other. Regarding the transverse axes, FIG. 14A illustrates a ratio RFWHM (=FWHM/FWHMref) of a full width at half maximum FWHM of each flow velocity waveform to a full width at half maximum FWHMref of the reference flow velocity waveform; FIG. 14B illustrates a ratio REf (1/RFWHM) of an inverse number (1/FWHM) of a full width at half maximum of each flow velocity waveform to an inverse number (1/FWHMref) of the full width at half maximum FWHMref of the reference flow velocity waveform; and FIG. 14C illustrates a ratio RAR (=(ΔUm/FWHM)/(ΔUmref/FWHMref)) of a ratio between the flow velocity maximum amplitude ΔUm and the full width at half maximum FWHM of each flow velocity waveform to a ratio between the flow velocity maximum amplitude ΔUmref and the full width at half maximum FWHMref of the reference flow velocity waveform.

Of the longitudinal axes of each of FIGS. 14A to 14C, the left axis expresses a cut depth, and the right axis expresses a cut volume.

In FIGS. 14A to 14C, a white plotted point indicates a case of the reference flow velocity waveform.

In FIG. 14A, both of the cut depth and the cut volume are reduced according to an increase in the ratio RFWHM. The cut volume is reduced more than the cut depth, and it can be seen that a change width thereof is large. In FIGS. 14B and 14C, both of the cut depth and the cut volume increase according to increases in the ratio REf and the ratio RAR. The cut volume increases more than the cut depth, and it can be seen that a change width thereof is large.

In other words, it can be seen that, if the maximum flow velocity Um of the main jet 3 is increased so that the entire flow velocity waveform has a steep shape in a state in which the duration T and the outflow mass M are fixed, the cut depth and the cut volume can be increased, and, if the maximum flow velocity Um is reduced so that the entire flow velocity waveform has a gentle shape, the cut depth and the cut volume can be reduced. This indicates that the cut depth and the cut volume can be changed by changing slow and rapid increasing tendencies of a rising waveform shape of the drive voltage waveform.

Figure 15A:
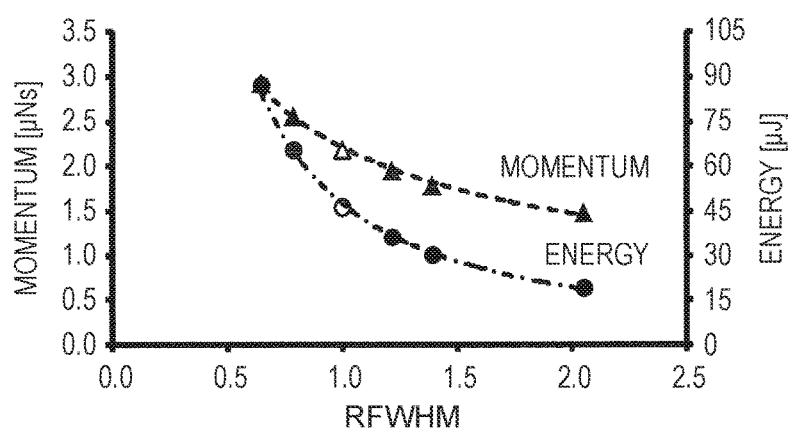
FIGS. 15A to 15C are diagrams illustrating simulation results of momentum and energy in a case where a full width at half maximum of a flow velocity waveform is changed.
Figure 15B:
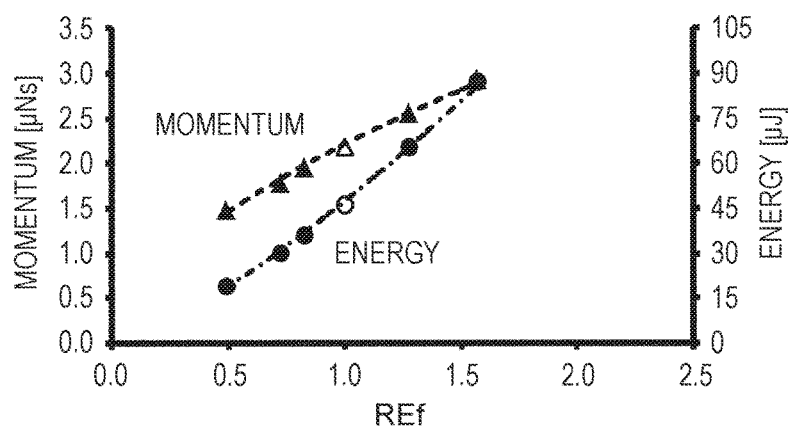
Figure 15C:
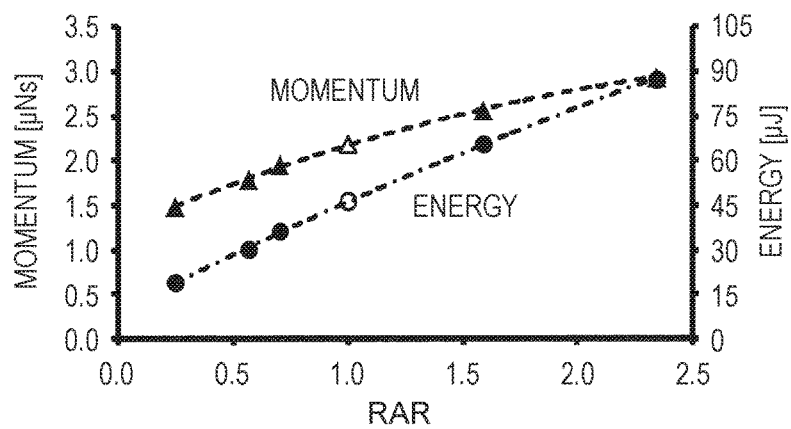

Next, FIGS. 15A to 15C illustrate calculation results of the momentum P and the energy E for the above six levels of the flow velocity waveform. Transverse axes of FIGS. 15A to 15C respectively correspond to the transverse axes of FIGS. 14A to 14C, in which the transverse axis of FIG. 15A expresses the ratio RFWHM, the transverse axis of FIG. 15B expresses the ratio REf, and the transverse axis of FIG. 15C expresses the ratio RAR. A left longitudinal axis expresses the momentum P, and a right longitudinal axis expresses the energy E. In FIGS. 15A to 15C, a white plotted point indicates a case of the reference flow velocity waveform.

In FIG. 15A, both of the momentum P and the energy E are reduced according to an increase in the ratio RFWHM. The energy E is reduced more than the momentum P, and it can be seen that a change width thereof is large. In FIGS. 15B and 15C, both of the momentum P and the energy E increase according to increases in the ratio REf and the ratio RAR. The energy E increases more than the momentum P, and it can be seen that a change width thereof is large.

The change aspects of the momentum P and the energy E for the ratio RFWHM, the ratio REf, and the ratio RAR in FIGS. 15A to 15C very similarly correspond to the change aspects of the cut depth and the cut volume for the ratio RFWHM, the ratio REf, and the ratio RAR in FIGS. 14A to 14C. As described above, the cut depth and the cut volume are highly correlated with the momentum P or the energy E.

As described above, it can be seen that the cut depth or the cut volume can be effectively controlled by using, as a control parameter defining a drive voltage waveform, a rising waveform shape of the drive voltage waveform, more specifically, changes (gentleness and steepness) of an increasing tenency of a drive voltage, such as slow starting or rapid starting.

When a certain reference waveform is indicated by V (t) with a time point t as a variable, a rising waveform shape of the driving voltage waveform L11 may be specified according to the following Equation (7), for example.

$$Vp = \begin{cases} V(t) \cdot \left(\frac{Tprc}{Vc} \cdot \frac{V(t)}{t}\right)^{N-1} & \dots (0 \leq t \leq T_{prc}) \\ -(Vm - V(t)) \cdot \left(\frac{Tprc}{Vc} \cdot \frac{Vm - V(t)}{Vpr - t}\right)^{N-1} + Vm & \dots (Tprc \leq t \leq Tpr) \end{cases} \quad (7)$$

Here, Vp indicates a drive voltage, Vm indicates voltage amplitude, Tpr indicates a rising time, Vc indicates a drive voltage at an inflection point, and Tprc indicates a time point at the inflection point R (refer to FIG. 12). N is a positive number which is larger than "0 (zero)".

N in FIG. 12 is N in Equation (7). If N=1, a rising waveform shape of the driving voltage waveform L11 is caused to be the reference waveform. As N becomes larger than 1, the drive voltage waveform sharply rises relative to the reference waveform. Conversely, as N approaches 0 (zero) smaller than 1, the drive voltage waveform slowly rises relative to the reference waveform, and gradually comes close to a straight line connecting the rising start point r0 to the rising end point r1.

According to Equation (7), it can be seen that a rising waveform shape of the driving voltage waveform L11 can be controlled by changing the variable N. However, this is only an example, and other functions may be used.

Regarding a method of changing the variable N, another value correlated with the variable N may be defined instead of using the variable N as a control target value, and the value may be used as a control target value. For example, there may be a method of changing the variable N on the basis of the ratio RFWHM, the ratio REf, and the ratio RAR described above. In a rising waveform of the driving voltage waveform L11, an effective rising time Tpr10_90 is defined as time required to reach 90% of the voltage amplitude Vm from 10% thereof, any one of the following 1) to 3) may be used: 1) a ratio RTpr10_90 of an effective rising time Tpr10_90 of a desired drive voltage waveform to an effective rising time Tpr10_90ref of the reference drive voltage waveform, 2) an effective rising frequency REf10_90 which is an inverse number of the ratio RTpr10_90 of 1), and 3) an effective slew rate ratio RSR10_90 which is a ratio of an effective slew rate (=Vm10_90/Tpr10_90) of a desired drive voltage waveform to an effective slew rate (=Vm10_90/Tpr10_90ref) of the reference drive voltage waveform. Vm10_90 indicates a voltage from 10% of the voltage amplitude Vm to 90% thereof.

Meanwhile, the principles have been described, and, in the present embodiment, as operations performed by an operator during surgery, at least an operation of changing the energy E and an operation of changing a repetition frequency are received, a rising waveform shape causing the designated energy E to be obtained at the designated repetition frequency is determined, and driving of the piezoelectric element 45 is controlled. Therefore, a correspondence relationship among the energy E, the repetition frequency, and the rising waveform shape is generated as a data table in advance. Regarding a rising waveform shape stored in the data table, data regarding a shape may be stored, and, for example, values of N in Equation (7) may be used index values of the rising waveform shape. If a constant repetition frequency is preferably used, an operation of changing the repetition frequency may not be needed, and only an operation of changing the energy E may be received so that a rising waveform shape is determined.

As an index value of a rising waveform shape stored in the data table, for example, any one of the ratio RFWHM, the ratio REf, and the ratio RAR, or any one of the ratio RTpr10_90, the effective rising frequency ratio REf10_90, and the effective slew rate ratio RSR10_90 may be stored.

Embodiment 1

Figure 16:
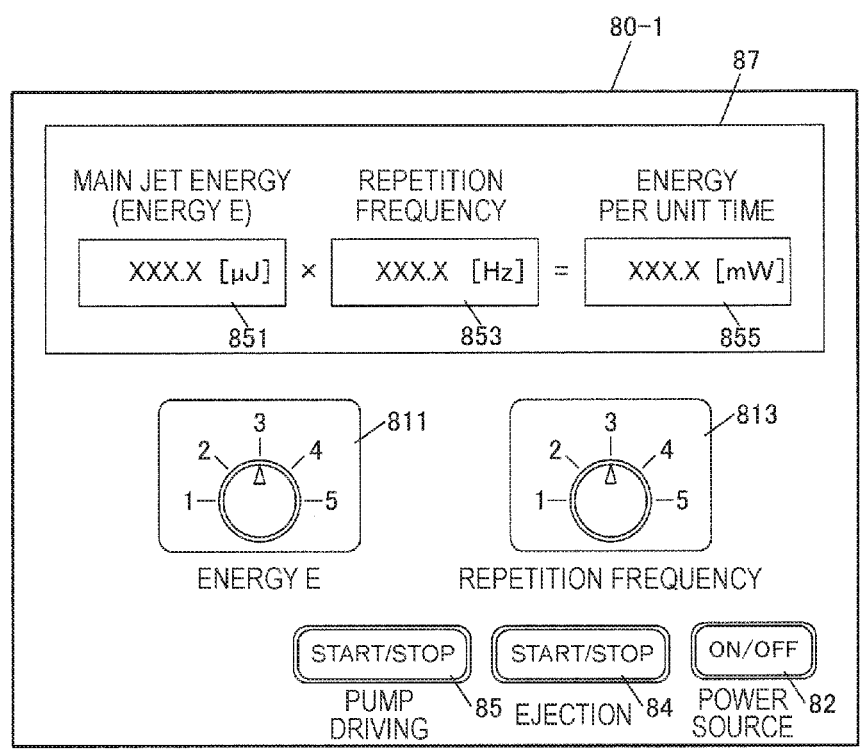
FIG. 16 is a diagram illustrating an operation panel of a liquid ejection control apparatus in Embodiment 1.

First, Embodiment 1 will be described. FIG. 16 is a diagram illustrating a configuration example of an operation panel 80-1 of a liquid ejection control apparatus 70-1 in Embodiment 1. As illustrated in FIG. 16, the operation panel 80-1 is provided with an energy dial 811 as a first operation unit, a repetition frequency dial 813 as a second operation unit, a power source button 82, an ejection button 84, a pump driving button 85, and a liquid crystal monitor 87.

The energy dial 811 is used to input an indication value (energy indication value) of the energy E as a first indication value, and is configured to allow dial positions in five steps, provided with scales such as "1" to "5", to be selected. An operator switches dial positions of the energy dial 811 so as to change the energy E in five steps. Energy indication values are allocated in advance to the respective dial positions so as to be increased by a predetermined level in proportion to a numerical value of a corresponding scale, for example. The number of steps of the dial positions is not limited to five steps, and may be set as appropriate, for example, three steps such as "large", "intermediate", and "small", or adjustment may be performed steplessly.

The repetition frequency dial 813 is used to input an indication value (repetition frequency indication value) of the repetition frequency as a second indication value, and is configured to allow dial positions in five steps, provided with scales such as "1" to "5", to be selected, in the same manner as the energy dial 811. The repetition frequency dial 813 may be configured to be provided with an activate switch for switching between validation and invalidation of an operation on the repetition frequency dial 813 assuming that the operator mainly performs an operation of changing the energy E. The operator switches dial positions of the repetition frequency dial 813 so as to change a repetition frequency (for example, several tens of Hz to several hundreds of Hz) of a drive voltage waveform which is repeatedly applied to the piezoelectric element 45, in five steps. Repetition frequency indication values are allocated in advance to the respective dial positions so as to be increased by a predetermined level in proportion to a numerical value of a corresponding scale, for example. The number of steps of the dial positions is not limited to five steps, and may be set as appropriate. The number of steps may be different from the number of steps of the energy dial 811. If the repetition frequency is fixed to a predetermined value, and thus an operation of changing the repetition frequency is not needed, the repetition frequency dial 813 is not required to be provided.

As mentioned above, in Embodiment 1, during surgery, the operator performs two operations such as the operation of changing the energy E using the energy dial 811 and the operation of changing the repetition frequency using the repetition frequency dial 813. The voltage amplitude and the rising frequency are fixed, and a rising waveform shape of a drive voltage causing the designated energy E to be obtained at the designated repetition frequency is generated as a data table in advance. Regarding a rising waveform shape stored in the data table, data regarding a shape may be stored, and an index value (for example, a value of N in Equation (7)) indicating a rising waveform shape may be stored.

The power source button 82 is used to switch between ON and OFF of a power source. The ejection button 84 is used to switch between ejection starting and ejection stoppage of a pulsed liquid jet, and provides the same function as that of the ejection pedal 83 illustrated in FIG. 1. The pump driving button 85 is used to switch between starting and stoppage of the supply of a liquid from the liquid feeding pump device 20 to the liquid ejection device 30.

In the operation panel 80-1, the liquid crystal monitor 87 displays a display screen on which the energy E, that is, energy [μJ] 851 of the main jet 3 corresponding to a single pulse, a repetition frequency [Hz] 853, and energy per unit time obtained by multiplying the energy by the repetition frequency, that is, power [mW] 855 are displayed, and the present values of the respective values (hereinafter, collectively referred to as "energy information") are updated and displayed. The present value of an energy indication value is displayed in the main jet energy 851, and a repetition frequency indication value is displayed in the repetition frequency 853. In a case where the repetition frequency dial 813 is not provided, and the repetition frequency is fixed to a predetermined value, the predetermined value is displayed in the repetition frequency 853. The operator can perform work on the basis of the display screen during surgery while recognizing the present values of the energy E, the repetition frequency, the energy (power) per unit time, and the like related to a pulsed liquid jet ejected from the liquid ejection opening 61.

There may be a configuration in which, during surgery, all of the three elements such as the energy E, the repetition frequency, and the energy per unit time are not necessary be displayed on the display screen as illustrated in FIG. 16, and only the energy E is displayed. At least one or both of the present rising frequency (or the rising time Tpr) and the voltage amplitude may be displayed in addition to the energy E, the repetition frequency, or the like. Display of each value is not limited to the display in numerical values illustrated in FIG. 16, and a value may be displayed in a meter form, or a change in the energy E, the repetition frequency, or the like due to a changing operation from starting of ejection of a pulsed liquid jet may be displayed in a graph form. A rising waveform shape determined by a dial position of the energy dial 811 or a dial position of the repetition frequency dial 813 may be displayed in a graph form, or an index value indicating a rising waveform shape may be displayed.

Figure 17:
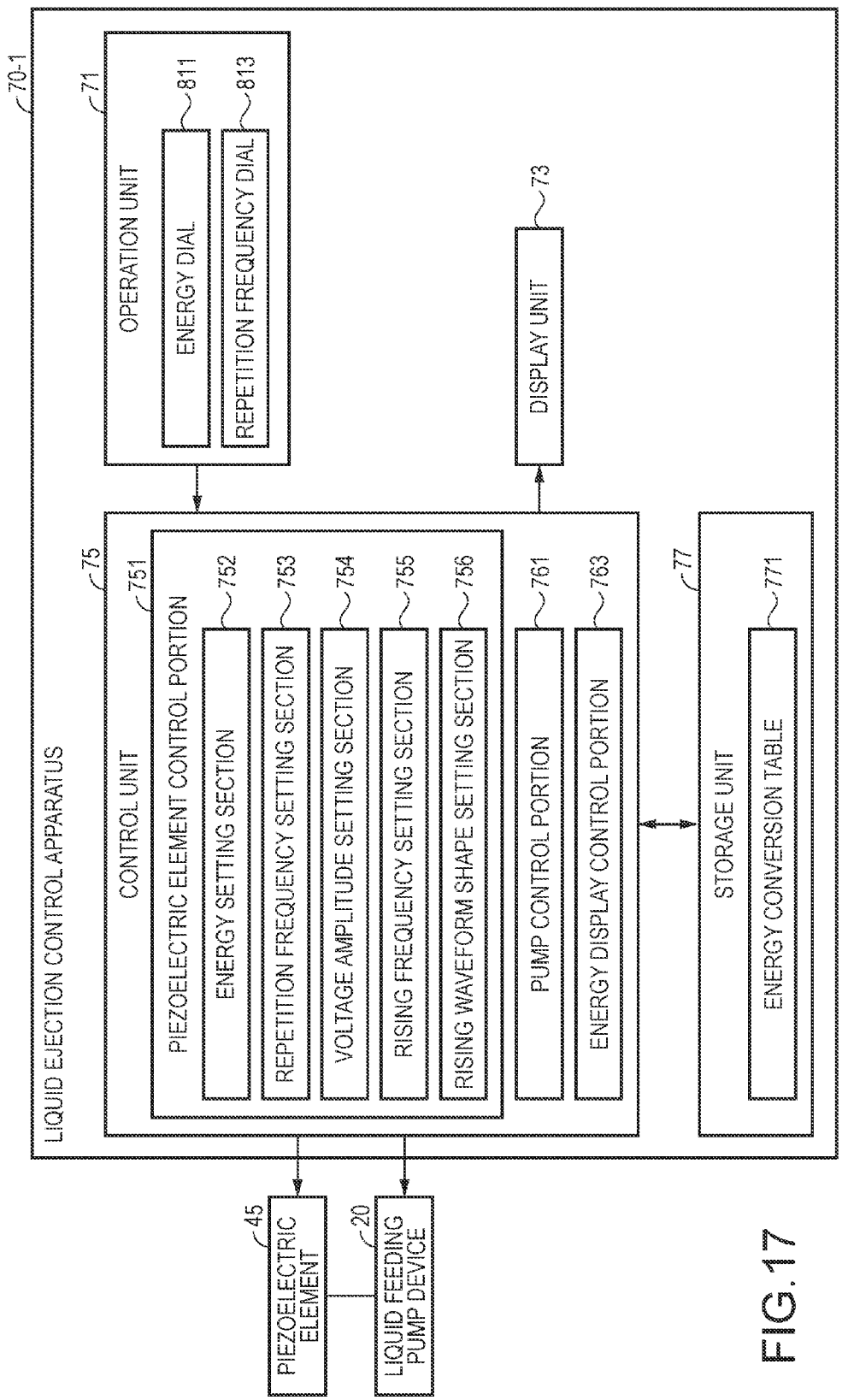
FIG. 17 is a block diagram illustrating a functional configuration example of the liquid ejection control apparatus in Embodiment 1.

FIG. 17 is a block diagram illustrating a functional configuration example of the liquid ejection control apparatus in Embodiment 1. As illustrated in FIG. 17, the liquid ejection control apparatus 70-1 includes an operation unit 71, a display unit 73, a control unit 75, and a storage unit 77.

The operation unit 71 is implemented by various switches such as a button switch, a lever switch, a dial switch, and a pedal switch, and an input device such as a touch panel, a track pad, and a mouse, and outputs an operation signal corresponding to an input operation to the control unit 75. The operation unit 71 is provided with the energy dial 811 and the repetition frequency dial 813. Although not illustrated in FIG. 17, the operation unit 71 includes the ejection pedal 83 illustrated in FIG. 1, and the power source button 82, the ejection button 84, and the pump driving button 85 on the operation panel 80-1 illustrated in FIG. 16.

The display unit 73 is implemented by a display device such as a liquid crystal display (LCD) or an electroluminescent (EL) display, and displays various screens such as the display screen illustrated in FIG. 16 on the basis of display signals input from the control unit 75. The display unit 73 corresponds to, for example, the liquid crystal monitor 87 illustrated in FIG. 16.

The control unit 75 is implemented by a microprocessor such as a central processing unit (CPU) or a digital signal processor (DSP), and a control device and a calculation device such as an application specific integrated circuit (ASIC) or a field programmable gate array (FPGA), and generally controls the respective portions of the liquid ejection system 1. The control unit 75 includes a piezoelectric element control portion 751, a pump control portion 761, and an energy display control portion 763 as a display control portion. The respective portions constituting the control unit 75 may be formed of hardware such as a dedicated module circuit.

The piezoelectric element control portion 751 includes an energy setting section 752, a repetition frequency setting section 753, a voltage amplitude setting section 754, a rising frequency setting section 755, and a rising waveform shape setting section 756. Above all, the voltage amplitude setting section 754 is a functional section which sets voltage amplitude of a drive voltage waveform to a predetermined fixed value. The rising frequency setting section 755 is a functional section which sets a rising frequency as a value regarding the rising time Tpr of a drive voltage waveform, and sets a rising frequency to a predetermined fixed value.

The energy setting section 752 sets energy corresponding to a dial position of the energy dial 811, and the set energy is used as a target value of energy of the main jet 3 to be ejected. The repetition frequency setting section 753 sets a repetition frequency corresponding to a dial position of the repetition frequency dial 813. The repetition cycle Tp is determined on the basis of the repetition frequency.

The rising waveform shape setting section 756 is a functional section which sets a rising waveform shape so that energy of a pulsed liquid jet becomes the energy set by the energy setting section 752. More specifically, in a drive voltage waveform in which the voltage amplitude set by the voltage amplitude setting section 754 is the maximum drive voltage, the rising time Tpr has a value corresponding to the rising frequency set by the rising frequency setting section 755, and the rising time Tpr has a value corresponding to the repetition frequency set by the repetition frequency setting section 753, a rising waveform shape of the drive voltage waveform, causing energy of the main jet 3 to be the energy set by the energy setting section 752 is set.

The piezoelectric element control portion 751 performs control of setting the drive voltage waveform by using the repetition frequency, the voltage amplitude, the rising frequency, and the rising waveform shape, set by the respective sections 753, 754, 755 and 756, and of applying a drive signal of the set waveform to the piezoelectric element 45. At this time, the piezoelectric element control portion 751 sets a waveform shape (falling waveform) of a falling portion of the drive voltage waveform variable in the way described in FIG. 10A so that a repetition frequency becomes the repetition frequency set by the repetition frequency setting section 753.

The pump control portion 761 outputs a drive signal to the liquid feeding pump device 20 so as to drive the liquid feeding pump device 20. The energy display control portion 763 performs control of displaying an energy indication value (that is, the present value of the energy E) allocated to a currently selected dial position of the energy dial 811, a repetition frequency indication value (that is, the present value of a repetition frequency) allocated to a currently selected dial position of the repetition frequency dial 813, and energy per unit time obtained by multiplying the indication values together, on the display unit 73.

The storage unit 77 is implemented by various integrated circuit (IC) memories such as a read only memory (ROM), a flash ROM, or a random access memory (RAM), or a storage medium such as a hard disk. The storage unit 77 stores in advance a program for operating the liquid ejection system 1 and thus realizing various functions of the liquid ejection system 1, data used during execution of the program, and the like, or temporarily stores data whenever a process is performed.

The storage unit 77 stores an energy conversion table 771. The energy conversion table 771 is a data table defining a rising waveform shape at each repetition frequency, causing predetermined energy.

FIG. 18 is a diagram illustrating a data configuration example of the energy conversion table 771. As illustrated in FIG. 18, the energy conversion table 771 is a data table in which a dial position (scale) of the energy dial 811, an energy indication value allocated to the dial position, a dial position (scale) of the repetition frequency dial 813, a repetition frequency indication value allocated to the dial position, and a rising waveform shape are correlated with each other, and the rising waveform shape at each repetition frequency causing the indicated energy E to be obtained is set in a state in which voltage amplitude and a rising frequency are set to predefined values. Data regarding the rising waveform shape stored in the energy conversion table 771 may be data regarding a shape, and may be an index value (for example, a value of N in Equation (7)) indicating a shape.

By referring to the energy conversion table 771, the rising waveform shape setting section 756 reads a rising waveform shape corresponding to a combination of currently selected dial positions of the energy dial 811 and the repetition frequency dial 813 from the energy conversion table 771 and sets the rising waveform shape, and reads a rising waveform shape corresponding to a combination of dial positions of the dials 811 and 813 from the energy conversion table 771 in a case where one of the energy dial 811 and the repetition frequency dial 813 is operated, and updates the set rising waveform shape.

Flow of Process

Figure 19:
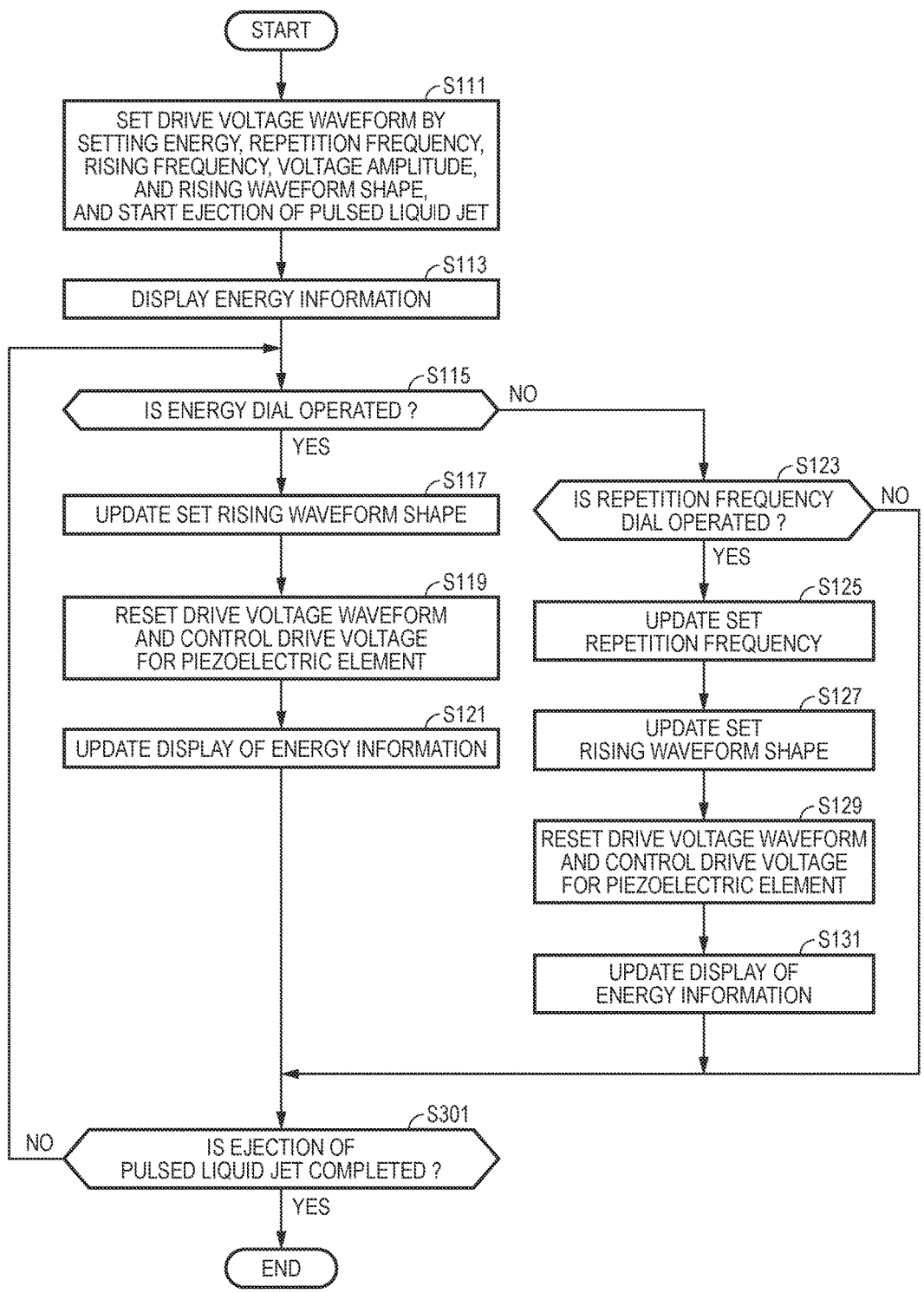
FIG. 19 is a flowchart illustrating a flow of a process performed by a control unit when a pulsed liquid jet is ejected in Embodiment 1.

FIG. 19 is a flowchart illustrating a flow of a process performed by the control unit 75 when a pulsed liquid jet is ejected. First, the pump control portion 761 drives the liquid feeding pump device 20, and the piezoelectric element control portion 751 drives the piezoelectric element 45 so as to start ejection of the pulsed liquid jet (step S111). At this time, the rising waveform shape setting section 756 acquires currently selected dial positions of the energy dial 811 and the repetition frequency dial 813, reads a rising waveform shape corresponding to a combination thereof from the energy conversion table 771, and sets the rising waveform shape. The voltage amplitude setting section 754 sets a predefined value as the voltage amplitude, the rising frequency setting section 755 sets a predefined value as the rising frequency. The energy setting section 752 reads an energy indication value allocated to the currently selected dial position of the energy dial 811 from the energy conversion table 771, and sets energy. The repetition frequency setting section 753 reads a repetition frequency indication value allocated to the currently selected dial position of the repetition frequency dial 813 from the energy conversion table 771, and sets a repetition frequency. The piezoelectric element control portion 751 sets a drive voltage waveform according to the set repetition frequency, voltage amplitude, rising frequency, and rising waveform shape, and applies a drive signal of the set drive voltage waveform to the piezoelectric element 45.

The energy display control portion 763 performs control of displaying energy information on the display unit (step S113). For example, the energy display control portion 763 reads the energy indication value allocated to the dial position of the energy dial 811 from the energy conversion table 771, and calculates energy per unit time corresponding to a product between the energy indication value and the repetition frequency indication value read in step S111. The energy display control portion 763 performs a display process of displaying a secondary screen on which the energy indication value, the repetition frequency indication value, and the energy per unit time are displayed as the energy information, on the display unit 73. The energy per unit time is not limited to being calculated when the energy information is displayed, and may be set in the energy conversion table 771 and may be read therefrom.

Next, the control unit 75 monitors an operation on the energy dial 811 in step S115 and monitors an operation on the repetition frequency dial 813 in step S123 until it is determined that the ejection of the pulsed liquid jet is completed due to an operation on the ejection pedal 83 or the ejection button 84 (NO in step S301).

In a case where the energy dial 811 is operated (YES in step S115), the rising waveform shape setting section 756 reads a rising waveform shape corresponding to a combination of a selected dial position of the energy dial 811 and the currently selected dial position of the repetition frequency dial 813 from the energy conversion table 771, and updates the set rising waveform shape (step S117). Thereafter, the piezoelectric element control portion 751 resets a drive voltage waveform according to the set repetition frequency, voltage amplitude, rising frequency, and rising waveform shape, and applies a drive signal of the reset drive voltage waveform to the piezoelectric element 45 (step S119).

The energy display control portion 763 performs control of reading an energy indication value allocated to the selected dial position from the energy conversion table 771, and updating the display of the display unit 73 (step S121).

On the other hand, in a case where the repetition frequency dial 813 is operated (YES in step S123), the repetition frequency setting section 753 reads a repetition frequency indication value allocated to a selected dial position from the energy conversion table 771, and updates the set repetition frequency (step S125). Next, the rising waveform shape setting section 756 reads a rising waveform shape corresponding to a combination of the selected dial position and the currently selected dial position of the energy dial 811 from the energy conversion table 771, and updates the set rising waveform shape (step S127). Thereafter, the piezoelectric element control portion 751 resets a drive voltage waveform according to the set repetition frequency, voltage amplitude, rising frequency, and rising waveform shape, and applies a drive signal of the reset drive voltage waveform to the piezoelectric element 45 (step S129).

The energy display control portion 763 performs control of reading a repetition frequency allocated to the selected dial position from the energy conversion table 771, and updating the display of the display unit 73 (step S131).

According to Embodiment 1, a rising waveform shape corresponding to each item of energy is set in advance, arising waveform shape which is optimal for achieving a cut depth and a cut volume corresponding to an operation sense is set on the basis of a correspondence relationship therebetween, and thus it is possible to control a drive voltage waveform for the piezoelectric element 45. For example, since the energy E is changed by an amount corresponding to a scale interval if the energy dial 811 is moved by one scale, it is possible to realize a cut depth or a cut volume suitable for a user's intention or operation sense and thus to improve convenience.

A repetition frequency can be changed so that the energy E has an energy indication value. Therefore, for example, if only a scale of the repetition frequency dial 813 is moved without moving a scale of the energy dial 811, a cut depth or a cut volume related to a pulsed liquid jet corresponding to a single pulse can be maintained to be constant, and a cutting speed can be adjusted as intended so as to be proportional to a repetition frequency so that convenience is improved.

Embodiment 2

Figure 20:
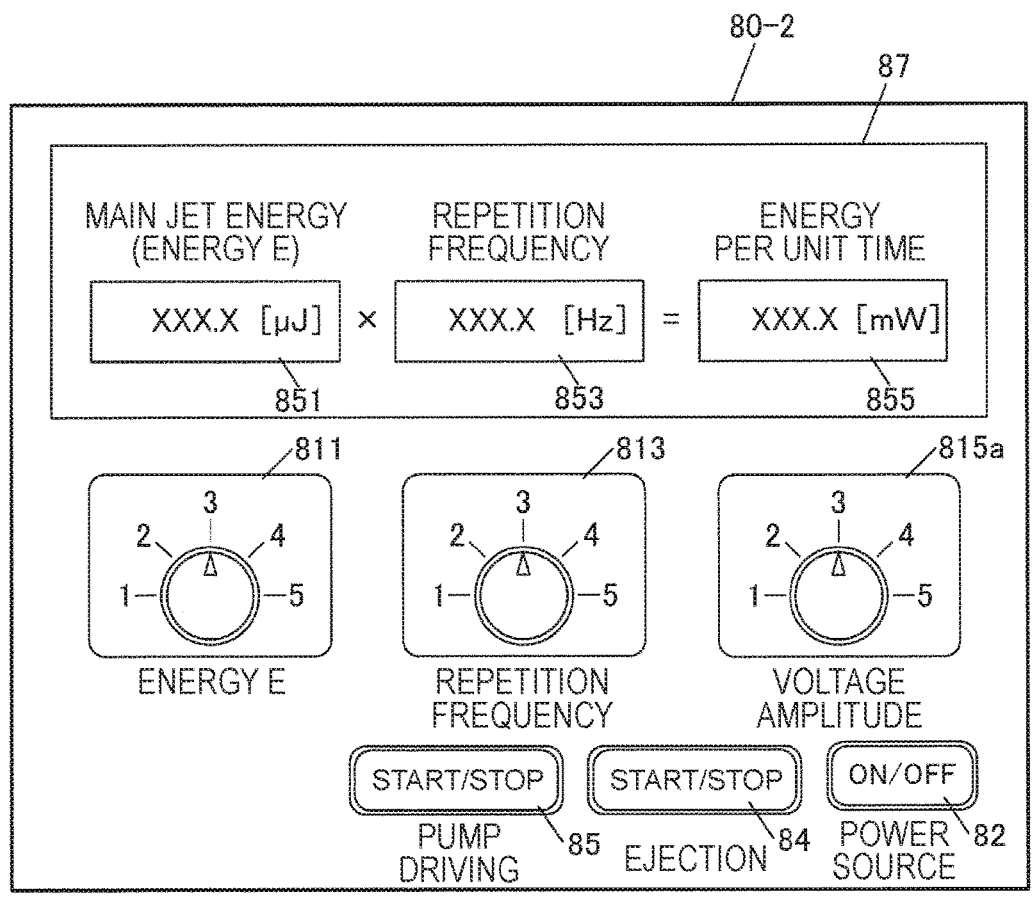
FIG. 20 is a diagram illustrating an operation panel of a liquid ejection control apparatus in Embodiment 2.

Next, Embodiment 2 will be described. The same constituent elements as in Embodiment 1 are given the same reference numerals, and a description will be made focusing on differences from Embodiment 1. FIG. 20 is a diagram illustrating a configuration example of an operation panel 80-2 of a liquid ejection control apparatus 70-2 in Embodiment 2. As illustrated in FIG. 20, the operation panel 80-2 is provided with an energy dial 811, a repetition frequency dial 813, a voltage amplitude dial 815a as a third operation unit, a power source button 82, an ejection button 84, a pump driving button 85, and a liquid crystal monitor 87.

The voltage amplitude dial 815a is used to input an indication value of voltage amplitude (voltage amplitude indication value) as a third indication value, and is configured to allow dial positions in five steps, provided with scales such as "1" to "5", to be selected. The voltage amplitude dial 815a may also be configured to be provided with an activate switch in the same manner as the repetition frequency dial 813. The operator switches dial positions of the voltage amplitude dial 815a so as to change voltage amplitude in five steps. Voltage amplitude indication values are allocated in advance to the respective dial positions so as to be increased by a predetermined level in proportion to a numerical value of a corresponding scale, for example. The number of steps of the dial positions is not limited to five steps, and may be set as appropriate. The number of steps may be different from the number of steps of the energy dial 811 or the repetition frequency dial 813.

As mentioned above, in Embodiment 2, during surgery, the operator performs three operations such as the operation of changing the energy E using the energy dial 811, the operation of changing the repetition frequency using the repetition frequency dial 813, and the operation of changing the voltage amplitude using the voltage amplitude dial 815a. A correspondence relationship among the energy E, the repetition frequency, the voltage amplitude, and the rising waveform shape is generated as a data table in advance.

Figure 21:
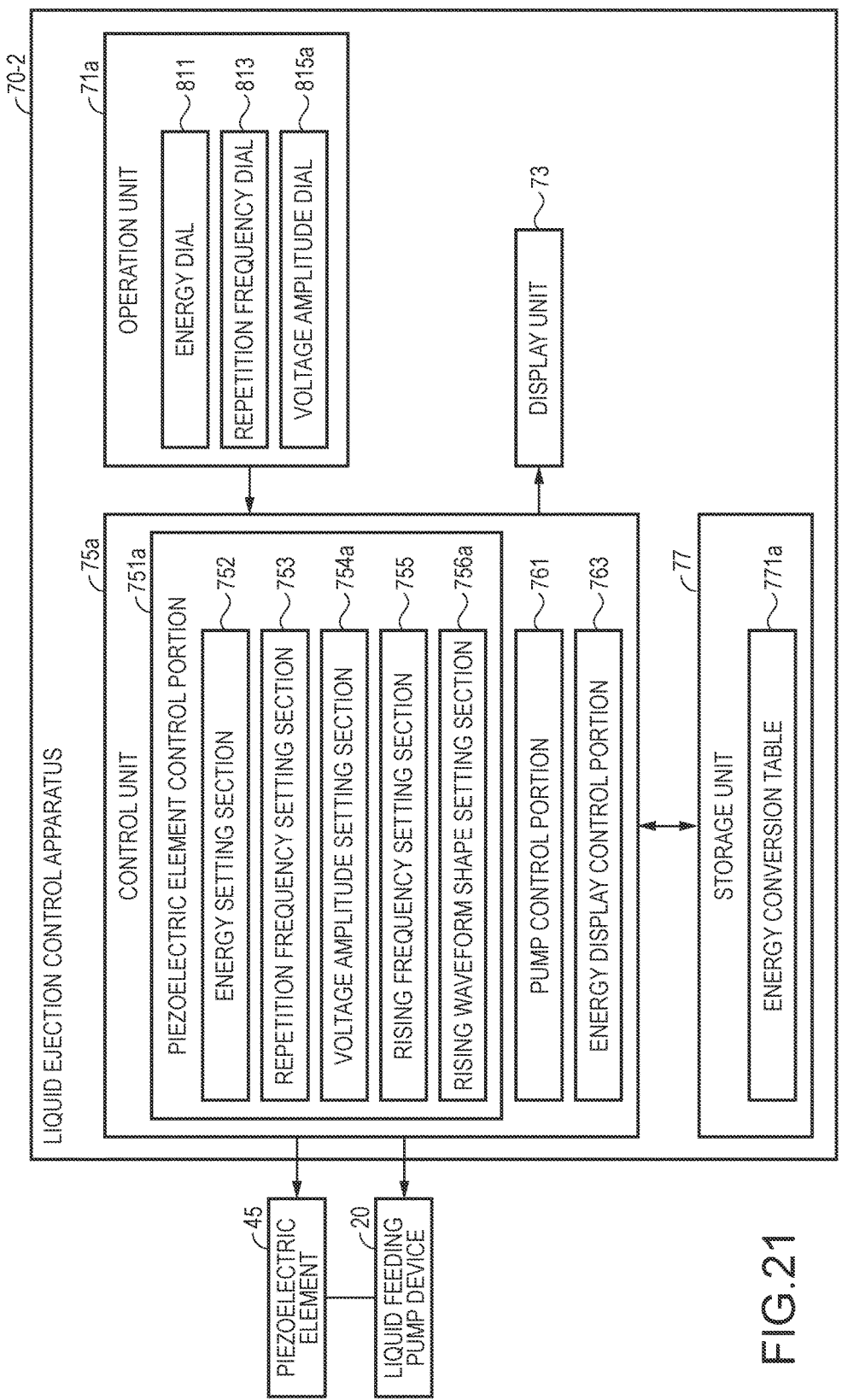
FIG. 21 is a block diagram illustrating a functional configuration example of the liquid ejection control apparatus in Embodiment 2.

FIG. 21 is a block diagram illustrating a functional configuration example of the liquid ejection control apparatus in Embodiment 2. As illustrated in FIG. 21, the liquid ejection control apparatus 70-2 is different from the liquid ejection control apparatus 70-1 of Embodiment 1 in that the operation unit 71 includes the voltage amplitude dial 815a, a voltage amplitude setting section 754a and a rising waveform shape setting section 756a included in a piezoelectric element control portion 751a and an energy conversion table 771a included in the storage unit 77.

The voltage amplitude setting section 754a reads voltage amplitude corresponding to a dial position of the voltage amplitude dial 815a from the energy conversion table 771a and sets the voltage amplitude.

The rising waveform shape setting section 756a is the same as in Embodiment 1 in that a rising waveform shape is set so that energy of a pulsed liquid jet becomes the energy set by the energy setting section 752, but is different from Embodiment 1 in that the energy is set by referring to the energy conversion table 771a.

FIG. 22 is a diagram illustrating a data configuration example of the energy conversion table 771a in Embodiment 2. As illustrated in FIG. 22, the energy conversion table 771a is a data table in which a dial position (scale) of the energy dial 811, an energy indication value allocated to the dial position, a dial position (scale) of the repetition frequency dial 813, a repetition frequency indication value allocated to the dial position, a dial position (scale) of the voltage amplitude dial 815a, a voltage amplitude indication value allocated to the dial position, and a rising waveform shape are correlated with each other. The energy conversion table 771a is a data table in which the rising waveform shape causing the indicated energy E to be obtained is set in correlation with a combination of the repetition frequency and the voltage amplitude in a state in which a rising frequency are set to a predefined value.

By referring to the energy conversion table 771a, the rising waveform shape setting section 756a reads a rising waveform shape corresponding to a combination of currently selected dial positions of the energy dial 811, the repetition frequency dial 813, and the voltage amplitude dial 815a from the energy conversion table 771a and sets the rising waveform shape, and reads a rising waveform shape corresponding to a combination of dial positions of the dials 811, 813 and 815a from the energy conversion table 771a in a case where any one of the energy dial 811, the repetition frequency dial 813, and the voltage amplitude dial 815a is operated, and updates the set rising waveform shape.

Flow of Process

Figure 23:
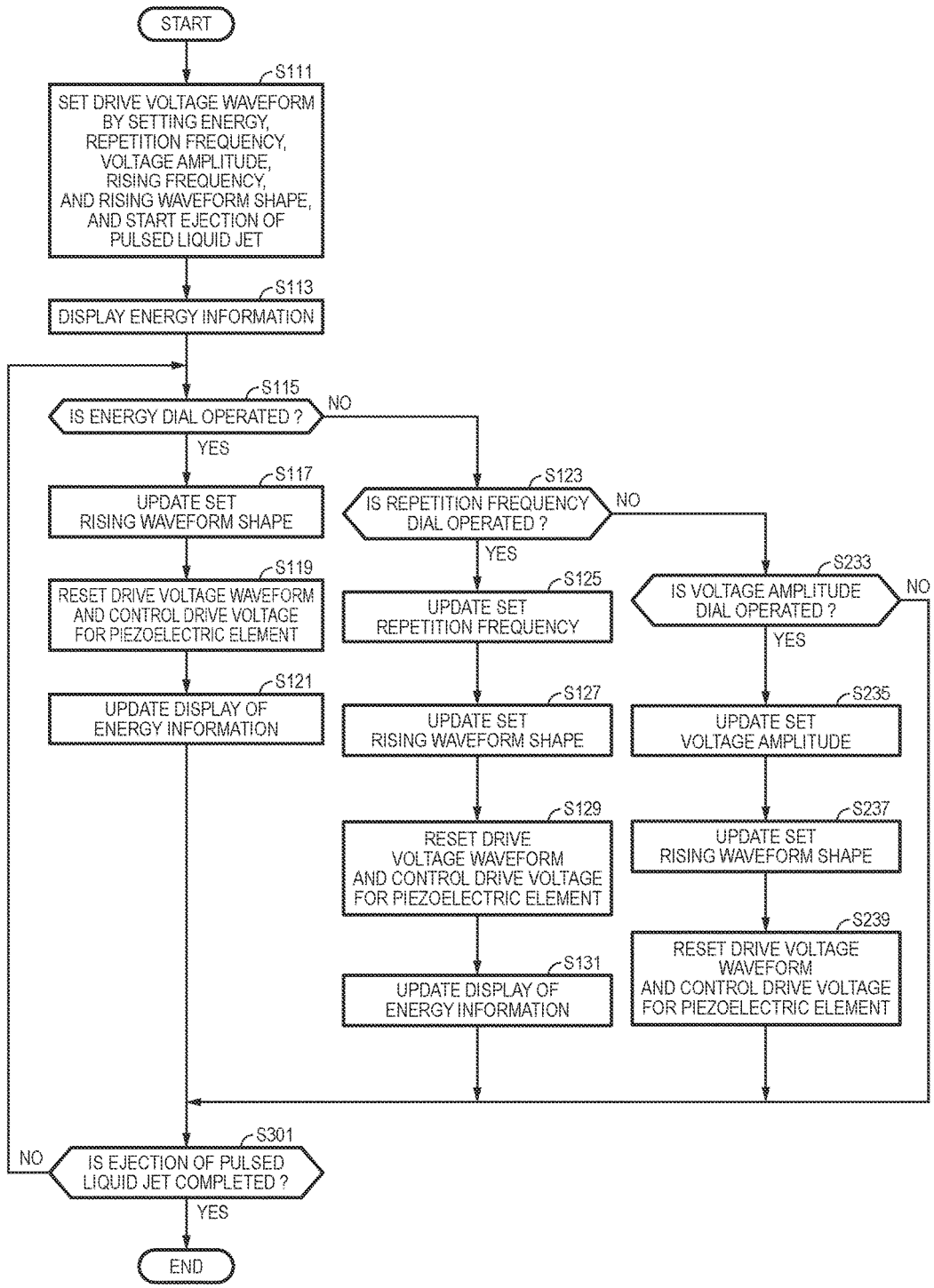
FIG. 23 is a flowchart illustrating a flow of a process performed by a control unit when a pulsed liquid jet is ejected in Embodiment 2.

FIG. 23 is a flowchart illustrating a flow of a process performed by a control unit 75a when a pulsed liquid jet is ejected in Embodiment 2. The same reference numerals are given to the same processing steps as those in FIG. 19.

In Embodiment 2, in step S111, the voltage amplitude setting section 754a reads a voltage amplitude indication value allocated to a currently selected dial position of the voltage amplitude dial 815a from the energy conversion table 771a, and sets voltage amplitude.

In step S233, an operation on the voltage amplitude dial 815a is monitored. In a case where the voltage amplitude dial 815a is operated (YES in step S233), the voltage amplitude setting section 754a reads a voltage amplitude indication value allocated to a selected dial position from the energy conversion table 771a and updates the set voltage amplitude (step S235). Next, the rising waveform shape setting section 756a reads a rising waveform shape corresponding to a combination with the selected dial position from the energy conversion table 771a, and updates the set rising waveform shape (step S237). Thereafter, the piezoelectric element control portion 751a resets a drive voltage waveform according to the set repetition frequency, voltage amplitude, and rising waveform shape, and applies a drive signal of the reset drive voltage waveform to the piezoelectric element 45 (step S239).

According to Embodiment 2, a correspondence relationship among the energy E, the repetition frequency, the voltage amplitude, and the rising waveform shape is set in advance, and a drive voltage waveform for the piezoelectric element 45 can be controlled so that the energy E has an energy indication value even if the voltage amplitude is changed.

Embodiment 3

Figure 24:
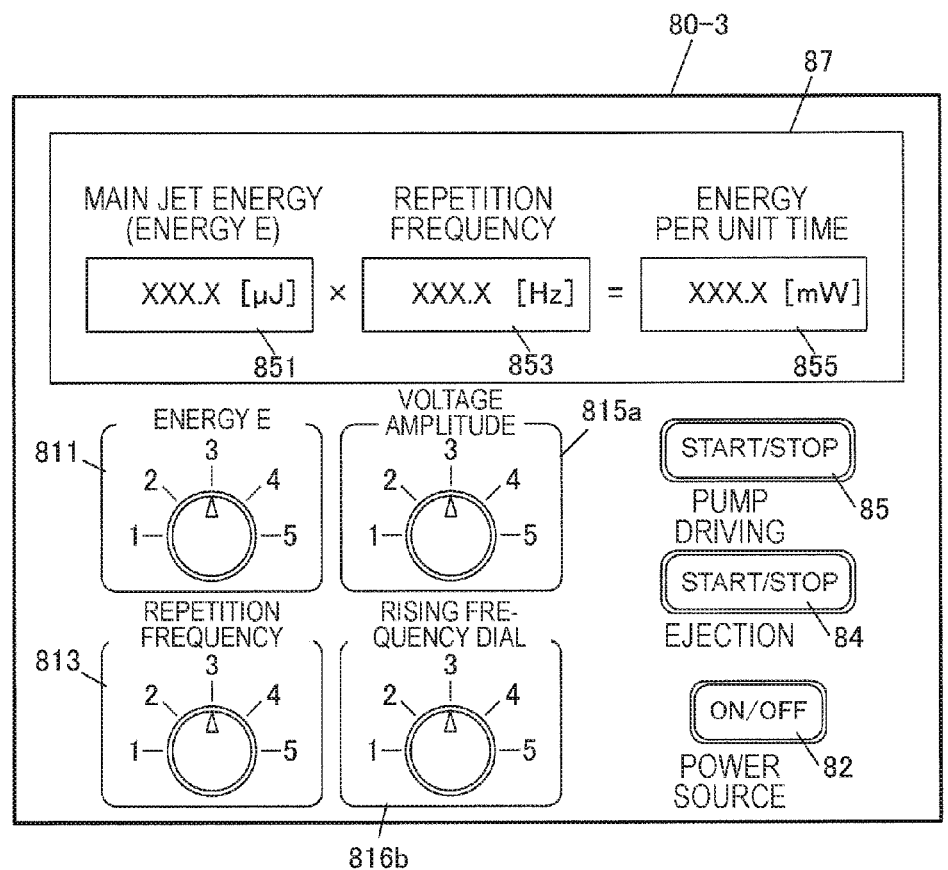
FIG. 24 is a diagram illustrating an operation panel of a liquid ejection control apparatus in Embodiment 3.

Next, Embodiment 3 will be described. The same constituent elements as in Embodiment 2 are given the same reference numerals, and a description will be made focusing on differences from Embodiment 2. FIG. 24 is a diagram illustrating a configuration example of an operation panel 80-3 of a liquid ejection control apparatus 70-3 in Embodiment 3. As illustrated in FIG. 24, the operation panel 80-3 is provided with an energy dial 811, a repetition frequency dial 813, a voltage amplitude dial 815a, a rising frequency dial 816b as a fourth operation unit, a power source button 82, an ejection button 84, a pump driving button 85, and a liquid crystal monitor 87.

The rising frequency dial 816b is used to input an indication value of a rising frequency (rising frequency indication value) as a fourth indication value, and is configured to allow dial positions in five steps, provided with scales such as "1" to "5", to be selected. The rising frequency dial 816b may also be configured to be provided with an activate switch in the same manner as the repetition frequency dial 813. The operator switches dial positions of the rising frequency dial 816b so as to change a rising frequency in five steps. Rising frequency indication values are allocated in advance to the respective dial positions so as to be increased by a predetermined level in proportion to a numerical value of a corresponding scale, for example. The number of steps of the dial positions is not limited to five steps, and may be set as appropriate. The number of steps may be different from the number of steps of the energy dial 811, the repetition frequency dial 813, or the voltage amplitude dial 815a.

As mentioned above, in Embodiment 3, during surgery, the operator performs four operations such as the operation of changing the energy E using the energy dial 811, the operation of changing the repetition frequency using the repetition frequency dial 813, the operation of changing the voltage amplitude using the voltage amplitude dial 815a, and the operation of changing the rising frequency using the rising frequency dial 816b. A correspondence relationship among the energy E, the repetition frequency, the voltage amplitude, the rising frequency, and the rising waveform shape is generated as a data table in advance.

Figure 25:
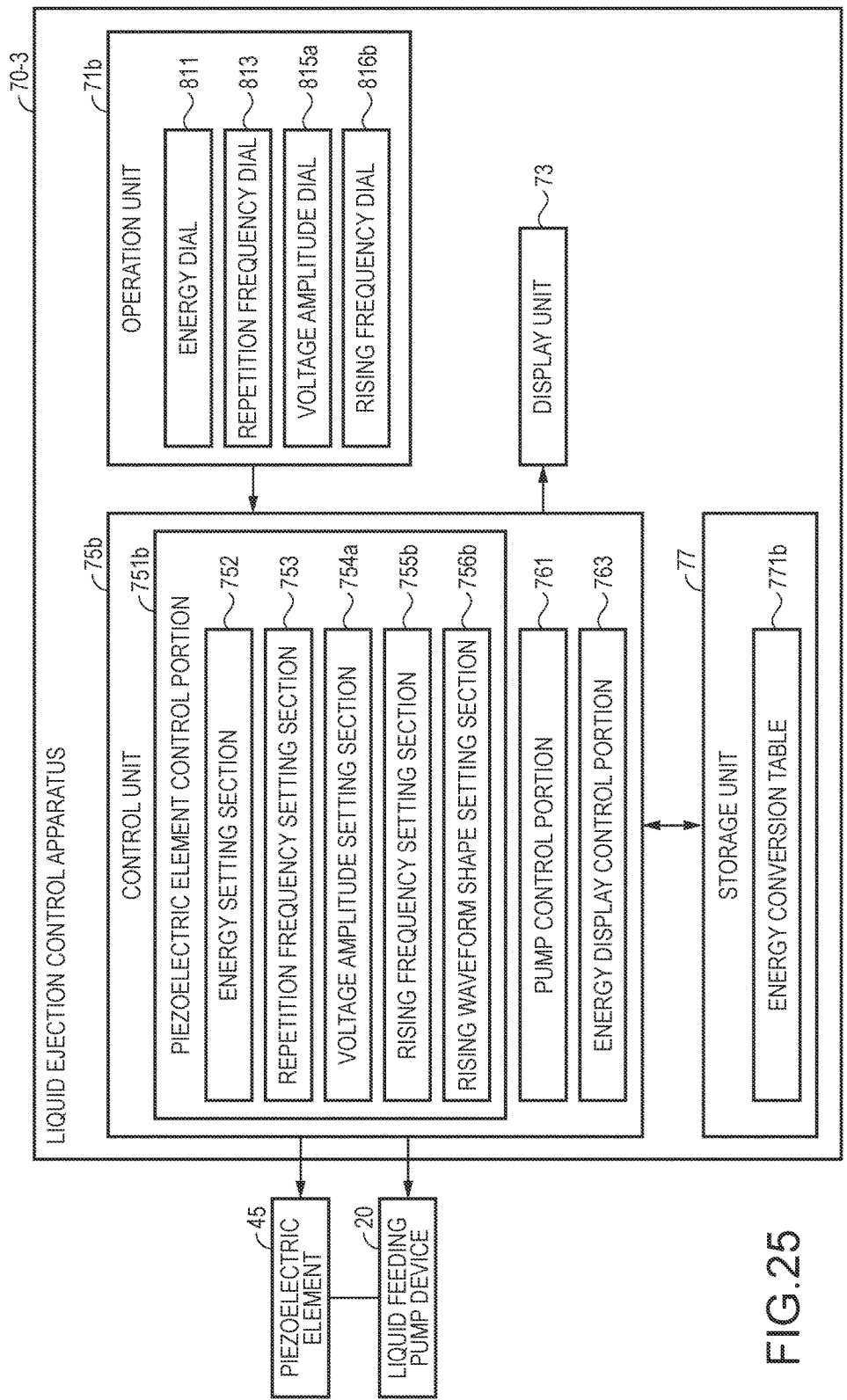
FIG. 25 is a block diagram illustrating a functional configuration example of the liquid ejection control apparatus in Embodiment 3.

FIG. 25 is a block diagram illustrating a functional configuration example of the liquid ejection control apparatus in Embodiment 3. As illustrated in FIG. 25, the liquid ejection control apparatus 70-3 is different from the liquid ejection control apparatus 70-2 of Embodiment 2 in that the operation unit 71 includes the rising frequency dial 816b, a rising frequency setting section 755b and a rising waveform shape setting section 756b included in a piezoelectric element control portion 751b and an energy conversion table 771b included in the storage unit 77.

The rising frequency setting section 755b reads a rising frequency corresponding to a dial position of the rising frequency dial 816b from the energy conversion table 771b, and sets the rising frequency.

The rising waveform shape setting section 756b is the same as in Embodiments 1 and 2 in that a rising waveform shape is set so that energy of a pulsed liquid jet becomes the energy set by the energy setting section 752, but is different from Embodiments 1 and 2 in that the energy is set by referring to the energy conversion table 771b.

FIG. 26 is a diagram illustrating a data configuration example of the energy conversion table 771b in Embodiment 3. As illustrated in FIG. 26, the energy conversion table 771b is a data table in which a dial position (scale) of the energy dial 811, an energy indication value allocated to the dial position, a dial position (scale) of the repetition frequency dial 813, a repetition frequency indication value allocated to the dial position, a dial position (scale) of the voltage amplitude dial 815a, a voltage amplitude indication value allocated to the dial position, a dial position (scale) of the rising frequency dial 816b, a rising frequency indication value allocated to the dial position, and a rising waveform shape are correlated with each other. The energy conversion table 771b is a data table in which the rising waveform shape causing the indicated energy E to be obtained is set in correlation with a combination of the repetition frequency, the voltage amplitude, and the rising frequency.

By referring to the energy conversion table 771b, the rising waveform shape setting section 756b reads a rising waveform shape corresponding to a combination of currently selected dial positions of the energy dial 811, the repetition frequency dial 813, the voltage amplitude dial 815a, and the rising frequency dial 816b from the energy conversion table 771b and sets the rising waveform shape. The rising waveform shape setting section 756b reads a rising waveform shape corresponding to a combination of dial positions of the dials 811, 813, 815a and 816b from the energy conversion table 771b in a case where any one of the energy dial 811, the repetition frequency dial 813, the voltage amplitude dial 815a, and the rising frequency dial 816b is operated, and updates the set rising waveform shape.

Flow of Process

Figure 27:
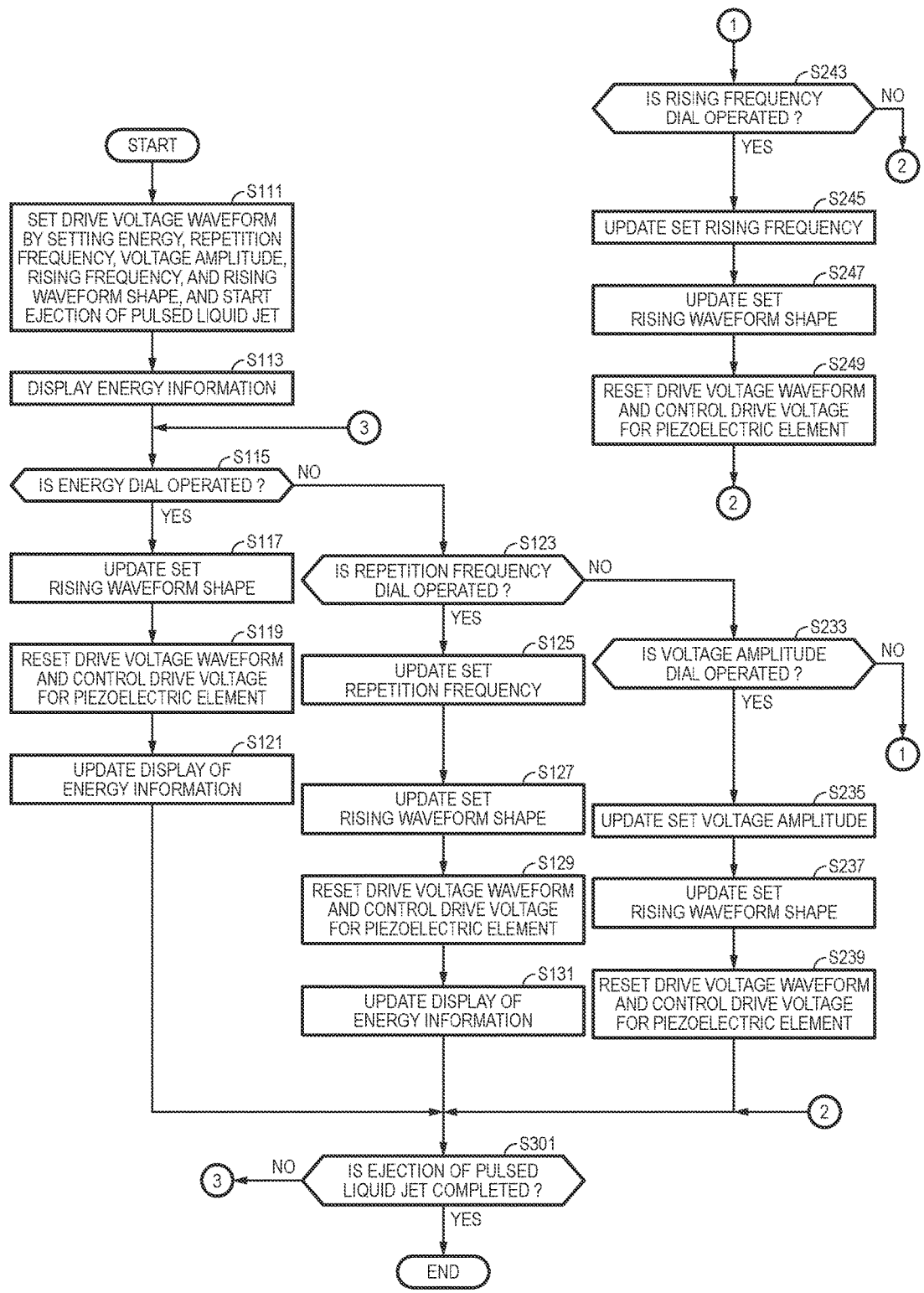
FIG. 27 is a flowchart illustrating a flow of a process performed by a control unit when a pulsed liquid jet is ejected in Embodiment 3.

FIG. 27 is a flowchart illustrating a flow of a process performed by a control unit 75b when a pulsed liquid jet is ejected in Embodiment 3. The same reference numerals are given to the same processing steps as those in FIG. 23.

In Embodiment 3, in step S111, the rising frequency setting section 755b reads a rising frequency indication value allocated to a currently selected dial position of the rising frequency dial 816b from the energy conversion table 771b, and sets a rising frequency.

In step S243, an operation on the rising frequency dial 816b is monitored. In a case where the rising frequency dial 816b is operated (YES in step S243), the rising frequency setting section 755b reads a rising frequency indication value allocated to a selected dial position from the energy conversion table 771b and updates the set rising frequency (step S245). Next, the rising waveform shape setting section 756b reads a rising waveform shape corresponding to a combination with the selected dial position from the energy conversion table 771b, and updates the set rising waveform shape (step S247). Thereafter, the piezoelectric element control portion 751b resets a drive voltage waveform according to the set repetition frequency, voltage amplitude, and rising waveform shape, and applies a drive signal of the reset drive voltage waveform to the piezoelectric element 45 (step S249).

According to Embodiment 3, a correspondence relationship among the energy E, the repetition frequency, the voltage amplitude, the rising frequency, and the rising waveform shape is set in advance, and a drive voltage waveform for the piezoelectric element 45 can be controlled so that the energy E has an energy indication value even if the rising frequency is changed.

Modification Examples

In the above-described embodiments, a description has been made a case of performing an operation of changing the energy E in steps by using the energy dial 811, a case of performing an operation of changing the repetition frequency in steps by using the repetition frequency dial 813, a case of performing an operation of changing the voltage amplitude in steps by using the voltage amplitude dial 815a, and a case of performing an operation of changing the rising frequency in steps by using the rising frequency dial 816b. In contrast, the respective dials 811, 813, 815a and 816b may be configured to be able to also adjust an energy indication value, a repetition frequency indication value, a voltage amplitude indication value, and a rising frequency indication value steplessly at an intermediate position between dial positions with scales.

In the above-described embodiments, a falling shape is set to be variable in order to change a repetition frequency as described with reference to FIG. 10A. In contrast, a repetition frequency may be changed simply by shrinking or broadening the entire drive voltage waveform in a time axis direction.

In the above-described embodiments, a rising frequency has been exemplified as a rising time index value. In contrast, the rising time Tpr may be used instead of the rising frequency.

The energy dial 811, the repetition frequency dial 813, the voltage amplitude dial 815a, and the rising frequency dial 816b are not limited to a case of being implemented by dial switches, and may be implemented by, for example, lever switches or button switches. If the display unit 73 is a touch panel, the dials may be implemented by key switches using software. In this case, a user touches the touch panel as the display unit 73, so as to input an energy indication value, a repetition frequency indication value, and a voltage amplitude indication value.

In the above-described Embodiment 2, a description has been made of an example in which voltage amplitude is set to be variable through a dial operation in addition to energy and a repetition frequency, but the repetition frequency may be fixed to a predefined value so as not to be variable.

Similarly, in the above-described Embodiment 3, a description has been made of an example in which a rising frequency is set to be variable through a dial operation in addition to energy, a repetition frequency, and voltage amplitude, but one or both of the repetition frequency and the voltage amplitude may be fixed to a predefined value so as not to be variable.

In the above-described embodiments, a description has been made of a configuration in which a pulsed liquid jet is ejected within a range in which the momentum is equal to or more than 2 nNs and is equal to or less than 2 mNs, and the kinetic energy is equal to or more than 2 nJ and is equal to or less than 200 mJ, but, more preferably, a pulsed liquid jet is ejected within a range in which the momentum is equal to or more than 20 nNs and is equal to or less than 200 μNs, and the kinetic energy is equal to or more than 40 nJ and is equal to or less than 10 mJ. With this configuration, it is possible to appropriately cut living tissue or a gel material.

In the above-described embodiments, a description has been made of a case where a drive voltage at the start point r0 is 0 (zero), the drive voltage at the start point r0 may not be 0 (zero). For example, in a form in which a drive voltage waveform is generated and applied in a state in which a predetermined voltage is biased, the biased voltage may be used as a voltage at the start point r0.

The entire disclosure of Japanese Patent Application No. 2015-185398 filed Sep. 18, 2015 is expressly incorporated by reference herein.

What is claimed is:

1. A liquid ejection control apparatus which applies a predetermined drive voltage waveform to a piezoelectric element, and controls repeated ejection of a pulsed liquid jet from a liquid ejection device which ejects a liquid in a pulse form by using the piezoelectric element, the apparatus comprising:
   a first operation unit that is used to input a first indication value related to kinetic energy of the pulsed liquid jet; and
   a control unit that controls the drive voltage waveform, and changes a waveform shape (hereinafter, referred to as a "rising waveform shape") related to rising of the drive voltage waveform so that the kinetic energy has the first indication value.

2. The liquid ejection control apparatus according to claim 1, further comprising:
   a second operation unit that is used to input a second indication value related to the number of times of ejection per unit time of the pulsed liquid jet,
   wherein the control unit controls the drive voltage waveform so that the number of times of ejection per unit time of the pulsed liquid jet becomes the second indication value.

3. A liquid ejection system comprising:
   the liquid ejection control apparatus according to claim 2;
   a liquid ejection device; and
   a liquid feeding pump.

4. The liquid ejection control apparatus according to claim 1, further comprising:
   a third operation unit that is used to input a third indication value related to voltage amplitude of the drive voltage waveform,
   wherein the control unit controls the voltage amplitude of the drive voltage waveform on the basis of the third indication value.

5. A liquid ejection system comprising:
   the liquid ejection control apparatus according to claim 4;
   a liquid ejection device; and
   a liquid feeding pump.

6. The liquid ejection control apparatus according to claim 1, further comprising:
   a fourth operation unit that is used to input a fourth indication value related to a rising time of the drive voltage waveform,
   wherein the control unit controls the rising time of the drive voltage waveform on the basis of the fourth indication value.

7. A liquid ejection system comprising:
   the liquid ejection control apparatus according to claim 6;
   a liquid ejection device; and
   a liquid feeding pump.

8. The liquid ejection control apparatus according to claim 1, further comprising:
   a display control unit that performs control of displaying the first indication value.

9. A liquid ejection system comprising:
   the liquid ejection control apparatus according to claim 8;
   a liquid ejection device; and
   a liquid feeding pump.

10. The liquid ejection control apparatus according to claim 1,
    wherein the liquid ejection device is controlled so that momentum of the pulsed liquid jet is equal to or more than 2 nanonewton seconds (nNs) and is equal to or less than 2 millinewton seconds (mNs), or kinetic energy of the pulsed liquid jet is equal to or more than 2 nanojoules (nJ) and is equal to or less than 200 millijoules (mJ).

11. A liquid ejection system comprising:
    the liquid ejection control apparatus according to claim 10;
    a liquid ejection device; and
    a liquid feeding pump.

12. The liquid ejection control apparatus according to claim 1,
    wherein the liquid ejection device is controlled so that living tissue is cut with the pulsed liquid jet.

13. A liquid ejection system comprising:
    the liquid ejection control apparatus according to claim 12;
    a liquid ejection device; and
    a liquid feeding pump.

14. A liquid ejection system comprising:
    the liquid ejection control apparatus according to claim 1;
    a liquid ejection device; and
    a liquid feeding pump.

15. A control method of applying a predetermined drive voltage waveform to a piezoelectric element, and controlling repeated ejection of a pulsed liquid jet from a liquid ejection device which ejects a liquid in a pulse form by using the piezoelectric element, the method comprising:
    inputting a first indication value related to kinetic energy of the pulsed liquid jet; and
    changing a waveform shape related to rising of the drive voltage waveform so that the kinetic energy has the first indication value.

* * * * *